(12) United States Patent
Firth et al.

(10) Patent No.: US 9,856,189 B2
(45) Date of Patent: *Jan. 2, 2018

(54) METHODS OF MAKING HIGH-WEIGHT ESTERS, ACIDS, AND DERIVATIVES THEREOF

(71) Applicant: Elevance Renewable Sciences, Inc., Woodridge, IL (US)

(72) Inventors: Bruce Firth, Buffalo Grove, IL (US); Brian M. Pease, Aurora, IL (US); Alexander D. Ilseman, Chicago, IL (US); Garrett Zopp, Crystal Lake, IL (US); Timothy A. Murphy, Yorkville, IL (US); Robin Weitkamp, Batavia, IL (US); Michelle Morie-Bebel, Naperville, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,784

(22) Filed: Jun. 20, 2016

(65) Prior Publication Data

US 2016/0362555 A1    Dec. 15, 2016

Related U.S. Application Data

(63) Continuation of application No. 14/678,123, filed on Apr. 3, 2015, now Pat. No. 9,388,098, which is a
(Continued)

(51) Int. Cl.
*C07C 6/02* (2006.01)
*C08L 91/06* (2006.01)
(Continued)

(52) U.S. Cl.
CPC .............. *C07C 6/02* (2013.01); *C07C 6/04* (2013.01); *C07C 29/132* (2013.01); *C07C 67/03* (2013.01);
(Continued)

(58) Field of Classification Search
None
See application file for complete search history.

(56) References Cited

U.S. PATENT DOCUMENTS 4,078,012 A * 3/1978 Blewett ............... B01J 31/0259
502/102
4,496,758 A * 1/1985 Blewett ................. C07C 67/293
554/153

(Continued)

OTHER PUBLICATIONS

Mol, J.C., Catalytic metathesis of unsaturated fatty acid esters and oils, 2004, Topics in Catalysis, vol. 27, Nos. 1-4, pp. 97-104.*

(Continued)

*Primary Examiner* — Yate K Cutliff
(74) *Attorney, Agent, or Firm* — Kilpatrick Townsend & Stockton LLP

(57) ABSTRACT

Methods and compositions are provided for refining natural oils and for producing high-weight esters, high-weight acids, and/or high-weight derivatives thereof, wherein the compositions are made by cross-metathesizing low-weight unsaturated esters or low-weight unsaturated acids having hydrocarbon chain lengths less than or equal to C24 with an olefin feedstock, thereby forming a metathesized product composition including high-weight esters or high-weight acids having hydrocarbon chain lengths greater than C18, wherein at least a portion of the hydrocarbon chain lengths in the metathesized product are larger than the hydrocarbon chain lengths in the starting feedstock.

9 Claims, 3 Drawing Sheets

Related U.S. Application Data continuation of application No. PCT/US2013/063870, filed on Oct. 8, 2013, and a continuation-in-part of application No. 13/647,825, filed on Oct. 9, 2012, now Pat. No. 8,735,640.

(60) Provisional application No. 61/861,345, filed on Aug. 1, 2013.

(51) Int. Cl.
| | |
|---|---|
| *C07C 6/04* | (2006.01) |
| *C07C 29/132* | (2006.01) |
| *C11C 3/12* | (2006.01) |
| *C11B 3/00* | (2006.01) |
| *C11C 3/00* | (2006.01) |
| *C07C 67/03* | (2006.01) |
| *C07C 67/343* | (2006.01) |
| *C07C 67/02* | (2006.01) |
| *C10G 29/20* | (2006.01) |
| *C10G 45/00* | (2006.01) |
| *C10G 45/58* | (2006.01) |
| *C10G 50/00* | (2006.01) |
| *C10G 65/04* | (2006.01) |
| *C10G 69/12* | (2006.01) |
| *C10L 1/02* | (2006.01) |
| *C10L 1/08* | (2006.01) |
| *C10G 3/00* | (2006.01) |

(52) U.S. Cl.
CPC ............ *C07C 67/343* (2013.01); *C08L 91/06* (2013.01); *C11B 3/00* (2013.01); *C11C 3/003* (2013.01); *C11C 3/12* (2013.01); *C07C 67/02* (2013.01); *C10G 3/42* (2013.01); *C10G 29/205* (2013.01); *C10G 45/00* (2013.01); *C10G 45/58* (2013.01); *C10G 50/00* (2013.01); *C10G 65/043* (2013.01); *C10G 69/123* (2013.01); *C10G 2300/1014* (2013.01); *C10G 2300/1018* (2013.01); *C10G 2300/1088* (2013.01); *C10G 2300/30* (2013.01); *C10G 2400/02* (2013.01); *C10G 2400/04* (2013.01); *C10G 2400/08* (2013.01); *C10G 2400/20* (2013.01); *C10G 2400/22* (2013.01); *C10L 1/02* (2013.01); *C10L 1/026* (2013.01); *C10L 1/08* (2013.01); *Y02P 30/20* (2015.11)

(56) References Cited

U.S. PATENT DOCUMENTS

| | | | | |
|---|---|---|---|---|
| 4,500,359 | A * | 2/1985 | Woods | A61K 8/06 106/270 |
| 2003/0065233 | A1* | 4/2003 | Fuji | C07C 1/20 585/639 |
| 2007/0161832 | A1* | 7/2007 | Myllyoja | C11B 13/00 585/7 |
| 2011/0113679 | A1* | 5/2011 | Cohen | C10G 45/00 44/388 |
| 2012/0271089 | A1* | 10/2012 | Wright | B01J 37/06 585/640 |
| 2013/0344012 | A1* | 12/2013 | Cohen | C11C 3/00 424/59 |

OTHER PUBLICATIONS

McKetta, J.J., Encyclopedia of Chemical Processing and Design, Alpha-Olefins, K.L. Lindsay, 1977, vol. 2, pp. 482-484 (6 pages).*

* cited by examiner

METHODS OF MAKING HIGH-WEIGHT ESTERS, ACIDS, AND DERIVATIVES THEREOF

CROSS-REFERENCE TO RELATED APPLICATIONS

The present application is a continuation of U.S. patent application Ser. No. 14/678,123, filed Apr. 3, 2015, which issued as U.S. Pat. No. 9,388,098 on Jul. 12, 2016, which is a continuation of PCT international application No. PCT/US2013/063870, filed Oct. 8, 2013, designating the United States, which claims the benefit of priority of U.S. Provisional Application No. 61/861,345, filed Aug. 1, 2013, and U.S. patent application Ser. No. 13/647,825, filed Oct. 9, 2012. The disclosures of the foregoing three applications are hereby incorporated by reference in their entireties as though fully set forth herein.

BACKGROUND

Montan wax, also known as lignite wax, LP wax and/or S wax, is a hard wax obtained by solvent extraction of lignite or brown coal (sub-bituminous coal). As it has been preserved in the coal, it is really fossilized plant wax. The earliest production on a commercial scale was in Germany during the latter half of the nineteenth century, and Germany continues to supply the majority of the world's production of montan wax. The composition of montan wax depends on the material from which it is extracted, but all contain varying amounts of wax, resin, and asphalt. Resins are removed by extraction with solvents (e.g., diethyl ether, acetone). The wax component of montan is a mixture of long chain (C24-C30) esters (62-68 wt %), long-chain acids (22-26 wt %), and long chain alcohols, ketones, and hydrocarbons (7-15 wt %). Montan has to go through an extensive chromic acid treatment to be refined, which process, for example, had been banned in California.

Montan wax is hard and brittle and has a high melt point; its properties are similar to those of natural plant waxes such as carnauba, which it can replace. Carbon papers were the largest consumer of crude montan wax. Currently the highest use of montan wax is in car polishes (30%). Additional applications include personal care applications, shoe polishes, electrical insulators, and lubricants in plastics and paper industry. Montan wax in polishes improves scuff resistance, increases water repellence, and imparts high gloss. Depending on refining and derivatization, waxes with different properties can be obtained from montan wax. Because montan wax is extracted from brown coal, the crude wax requires extensive and costly cleaning. Recently the concentration of extractable montan wax in the German rock formations has decreased. Due to the uncertainty of supply and varying nature of the product, as well as its relative high cost, a substitute for montan wax having similar properties to montan wax is desirable.

Carnauba wax is derived from the palm tree, whose wax-producing stands grow almost exclusively in the semi-arid northeast section of Brazil. Carnauba wax forms on the fronds of the palm, and is removed by cutting the fronds, drying, and mechanically removing the wax. Impurities are removed from the wax by melting and filtering or centrifuging. Wide fluctuations in price and availability have caused markets served by carnauba wax to seek replacements. The major components of carnauba wax are aliphatic and aromatic esters of long-chain alcohols and acids, with smaller amounts of free fatty acids and alcohols, and resins. Carnauba wax is very hard, with a penetration of 2 dmm at 25° C. and only 3 dmm at 43.3° C. Certain grades of carnauba wax may also have one of the higher melting points for the natural waxes. For example, one grade of carnauba wax has a melting point of 84° C., with a viscosity of 3960 cSt at 98.9° C., an acid number of 8, and a saponification number of 80.

The hardness and high melting point, when combined with its ability to disperse pigments such as carbon black, allows Carnauba wax increasing use in the thermal printing inks. Carnauba wax is also widely used as organic structurant to gel organic solvents and oils, making the wax a valuable component of solvent and oil paste formulations. Carnauba wax polishes to a high gloss and thus is widely used as a polishing agent for items such as leather, candies, and pills. Other uses include cosmetics and investment casting applications (e.g., copper alloys, cast copper alloys).

Candelilla wax is harvested from shrubs in the Mexican states of Coahuila and Chihuahua and, to a very small degree, in the Big Bend region of Texas in the United States. The entire mature plant is uprooted and immersed in boiling water acidified with sulfuric acid. The wax floats to the surface and is filtered. The major components of candelilla wax are hydrocarbons, esters of long-chain alcohols and acids, long-chain alcohols, sterols, and neutral resins, and long-chain acids. Candelilla wax may have a melting point of 70° C., a penetration of 3 dmm at 25° C., an acid number of 14, and a saponification number of 55. Principal markets for Candelilla include cosmetics, foods, and pharmaceuticals.

Ouricury wax is a brown wax obtained from the fronds of a palm tree, which grows in Brazil. Ouricury is difficult to harvest, as it does not flake off the frond as does carnauba wax, and therefore is scraped off. Ouricury is sometimes used as a replacement for carnauba in applications that do not require a light-colored wax. Rice-bran wax is extracted from crude rice-bran oil. It can be degummed, the fatty acid content reduced by solvent extraction, and bleached. The wax is primarily composed of esters of lignoceric acid (43 wt %), behenic acid (16 wt %), and C22-C36 alcohols (28 wt %).

Beeswax is a natural wax produced in the beehive of honeybees, and includes a mixture of several compounds, such as fatty acids and various long chain alcohols. Beeswax may include palmitate, palmitoleate, and oleate esters of long chain (C30-C32) aliphatic alcohols, with the ratio of triacontanyl palmitate to cerotic acid being approximately 6:1. Beeswax may have a melting point range of about 62-64° C. (144-147° F.), a flashpoint of about 204.4° C. (400° F.), and a density at 15° F. of about 958-970 kg/m$^3$.

Metathesis is a catalytic reaction that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

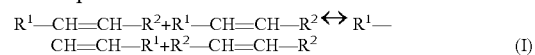

(I)

wherein $R^1$ and $R^2$ are organic groups.

Cross-metathesis may be represented schematically as shown in Equation II.

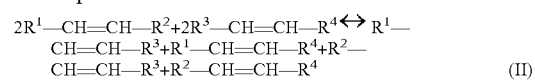

(II)

wherein $R^1$, $R^2$, $R^3$, and $R^4$ are organic groups.

In recent years, there has been an increased demand for environmentally friendly techniques for manufacturing materials derived from petroleum sources. For example, researchers have been studying the feasibility of manufacturing biofuels, waxes, plastics, and the like, using natural oil feedstocks, such as vegetable and seed-based oils. In one non-limiting example, metathesis catalysts are used to manufacture candle wax, as described in WO 2006/076364, which is herein incorporated by reference in its entirety. Metathesis reactions involving natural oil feedstocks offer promising solutions for today and for the future.

Natural oil feedstocks of interest include non-limiting examples such as natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Representative non-limiting examples of useful metathesis catalysts are provided below. Metathesis catalysts can be expensive and, therefore, it is desirable to improve the efficiency of the metathesis catalyst.

In certain instances, metathesis of natural oil feedstocks may provide a useful way to make chemical intermediates that may be difficult to make by other means. Or, in some other instances, metathesis of natural oil feedstocks may provide a useful way to make "green" alternatives to existing compounds or materials. Therefore, there is a continuing need to develop processes and systems that employ natural oil metathesis to make commercially and/or technically useful compounds and materials.

Additionally, there is a need for a natural oil fatty acid or ester wax that may completely substitute and/or replace other waxes (such as beeswax, Montan wax, Carnauba Wax, Candelilla Wax, or Ouricury Wax), or may be used as an extender for such waxes.

SUMMARY

Methods and systems are disclosed for refining natural oils and for producing high-weight esters and derivatives thereof.

In a first aspect, making high-weight esters or high-weight acids includes providing a starting feedstock including unsaturated esters and/or unsaturated acids, wherein a majority of the hydrocarbon chain lengths in the feedstock are less than or equal to C24. The method optionally includes hydrolyzing the unsaturated esters in the starting feedstock to form a hydrolyzed feedstock. The method further includes optionally transesterifying the starting feedstock or the hydrolyzed feedstock to form a transesterified feedstock. The method further includes cross-metathesizing the starting feedstock, hydrolyzed feedstock, or transesterified feedstock with an olefin feedstock in the presence of a metathesis catalyst, thereby forming a metathesized product including high-weight esters or high-weight acids having hydrocarbon chain lengths greater than C18, wherein at least a portion of the hydrocarbon chain lengths in the metathesized product are larger than the hydrocarbon chain lengths in the starting feedstock.

In certain embodiments, the method further includes agitating at least a portion of the metathesized product as it is cooled from an elevated temperature to ambient temperature to thereby alter at least one property of the metathesized product. In other embodiments, the method further includes reducing the high-weight esters to form a high-weight alcohol. In some embodiments, the method further includes transesterifying the high-weight alcohol with a fatty acid ester. In some embodiments, the starting feedstock includes a fatty acid ester having an unsaturated carbon-carbon bond at the C9-C10 position of the fatty acid ester, wherein the olefin feedstock includes a mixture of C16-C26 alpha-olefins, wherein the fatty acid ester is a C16-C18 fatty acid methyl ester, thereby forming a C40-C52 high-weight ester composition. In some embodiments, the method further includes blending the C40-C52 high-weight ester composition with a hydrocarbon feedstock and a free fatty acid feedstock, thereby forming a beeswax-like composition.

In certain embodiments, the method further includes transesterifying the high-weight esters with an alcohol. The starting feedstock may include a fatty acid ester having an unsaturated carbon-carbon bond at the C9-C10 position of the fatty acid ester, wherein the olefin feedstock includes a mixture of C16-C26 alpha-olefins, wherein the alcohol is a C16-C18 alcohol, thereby forming a C40-C52 high-weight ester composition. In some embodiments, the method further includes blending the C40-C52 high-weight ester composition with a hydrocarbon feedstock and a free fatty acid feedstock, thereby forming a beeswax-like composition.

In certain embodiments, the feedstock is selected from the group including monoacylglycerides, diacylglycerides, triacylglycerides, polyfunctional esters, and mixtures thereof. In other embodiments, the transesterified feedstock is formed by transesterifying the starting feedstock or the hydrolyzed feedstock in the presence of an alcohol. In yet other embodiments, the method further includes transesterifying the metathesized product subsequent to the cross-metathesizing step. In certain embodiments, the method further includes at least partially hydrogenating the high-weight esters or the high-weight acids.

In certain embodiments, the metathesized product composition includes at least 10 wt % high-weight esters or high-weight acids having hydrocarbon chain lengths of C22 to C60, or at least 40 wt % high-weight esters or high-weight acids having hydrocarbon chain lengths of C22 to C36.

In certain embodiments, the olefin feedstock is a mid-weight olefin, and, in some embodiments, an alpha olefin. In certain embodiments, the olefin feedstock is derived from one of the following: (1) a natural oil feedstock, (2) a fatty alcohol which is dehydrated, (3) a biological process that selectively produces olefins from natural occurring saturated hydrocarbon compounds, and (4) ethanol. In other embodiments, the olefin feedstock is derived from free fatty acid esters, wherein the free fatty acid esters are reduced to form a terminal alcohol, which is then catalytically dehydrated to form the olefin feedstock. In some embodiments, the free fatty acid esters include a mixture of C12-C18 esters. In other embodiments, the free fatty acid esters are derived from a natural oil feedstock which has been transesterified with an alcohol.

In certain embodiments, the method forms a high-weight ester or high-weight acid for use as a wax composition, detergent, surfactant, structurant, emollient, adhesive, lubricant, film, paint, paint stripper, coating, plasticizer, resin, binder, solvent, soil stabilization composition, chemical grouting composition, personal care product, biodiesel composition, crop protection product, oilfield drilling fluid, or chemical for oil recovery. In some embodiments, the wax composition has one or more of the following properties: (a) a drop point of 50-130° C.; (b) a needle penetration of 0-30 dmm at 25° C.; and (c) a saponification value of 50-250 mg KOH/g.

In a second aspect, the making high-weight esters or high-weight acids includes providing a natural oil triglyceride wherein a majority of the hydrocarbon chain lengths in the natural oil are less than or equal to C24. The method further includes providing an olefin feedstock. The method further cross-metathesizing the natural oil with the olefin feedstock in the presence of a metathesis catalyst to form a metathesized product composition including (i) olefins and (ii) triglycerides with extended chain esters, wherein the hydrocarbon chain lengths of the extended chain esters are greater than C18, wherein at least a portion of the hydrocarbon chain lengths in the metathesized product are larger than the hydrocarbon chain lengths in the natural oil feedstock. The method further includes separating the olefins in the metathesized product from the triglycerides with extended chain esters in the metathesized product.

In certain embodiments, the method further includes separating the olefins in the metathesized product from the triglycerides with extended chain esters in the metathesized product. In other embodiments, the method further includes at least partially hydrogenating the olefins or the triglycerides with extended chain esters in the metathesized product. In yet other embodiments, the method further includes at least partially hydrogenating the olefins and the triglycerides with extended chain esters in the metathesized product.

In certain embodiments, the method further includes transesterifying the triglycerides with extended chain esters with an alcohol to form high-weight esters. In some embodiments, the method further includes at least partially hydrogenating the high-weight esters. In some embodiments, the method further includes hydrolyzing the high-weight esters to form high-weight acids. In some embodiments, the method further includes at least partially hydrogenating the high-weight acids.

In certain embodiments, the method further includes agitating the metathesized product composition as it is cooled from an elevated temperature to ambient temperature to thereby alter at least one property of the metathesized product.

In certain embodiments, the olefin feedstock is a mid-weight olefin, and, in some embodiments, an alpha olefin. In certain embodiments, the olefin feedstock is derived from one of the following: (1) a natural oil feedstock, (2) a fatty alcohol which is dehydrated, (3) a biological process that selectively produces olefins from natural occurring saturated hydrocarbon compounds, and (4) ethanol. In other embodiments, the olefin feedstock is derived from free fatty acid esters, wherein the free fatty acid esters are reduced to form a terminal alcohol, which is then catalytically dehydrated to form the olefin feedstock. In some embodiments, the free fatty acid esters include a mixture of C12-C18 esters. In other embodiments, the free fatty acid esters are derived from a natural oil feedstock which has been transesterified with an alcohol.

In a third aspect, the method of refining a natural oil includes providing a feedstock including a natural oil (such as a natural oil glyceride). The method further includes providing a low-weight olefin or mid-weight olefin. The method further includes reacting the feedstock and the low-weight olefin or mid-weight olefin in a metathesis reactor in the presence of a metathesis catalyst to form a metathesized product including olefins and metathesized esters or glycerides. The method further includes separating the olefins in the metathesized product from the metathesized esters or glycerides in the metathesized product. The method further includes transesterifying the metathesized esters or glycerides in the presence of an alcohol to form a transesterified product (such as glycerin and fatty acid esters having no glycerin backbone). In certain embodiments, the reacting step is between the feedstock and the mid-weight olefin. In other embodiments, the reacting step is with a C6 to C14 low-weight olefin. In some embodiments, the low-weight olefin is selected from the group including 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some embodiments, the low-weight olefin is 3-hexene. In some embodiments, the low-weight olefin or mid-weight olefin is an alpha-olefin. In some embodiments, the natural oil is a natural oil glyceride, such as a natural oil triglyceride selected from the group including vegetable oils, algae oils, animal fats, and combinations thereof. In certain embodiments, the natural oil glyceride is a vegetable oil selected from the group including canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, castor oil, and combinations thereof. In certain embodiments, the alcohol is methanol or ethanol.

In certain embodiments, the method further includes self-metathesizing the low-weight olefin or mid-weight olefin in the presence of a second metathesis catalyst prior to the metathesis reaction with feedstock, forming a metathesized low-weight olefin or metathesized mid-weight olefin. In certain embodiments, the method further includes isomerizing the low-weight olefin, mid-weight olefin, metathesized low-weight olefin, or metathesized mid-weight olefin prior to the metathesis reaction with the feedstock. In other embodiments, the method further includes separating C10+ olefins from the olefin in the metathesized product. The C10+ olefins may be reacted with ethylene in the presence of a second metathesis catalyst. In yet other embodiments, the method further includes self-metathesizing the olefins in the metathesized product in the presence of a second metathesis catalyst. In any of these embodiments, the second metathesis catalyst may be a rhenium oxide catalyst or tungsten oxide catalyst.

In certain embodiments, the transesterified product includes C10 methyl esters and C12+ methyl esters, and further includes separating the C10 methyl esters from the C12+ methyl esters. In some embodiments, the method further includes reacting the C10 methyl esters with 1-butene in the presence of a metathesis catalyst and forming a product composition having C12 methyl esters. In some embodiments, the method further includes recycling a portion of the transesterified product to the metathesis reactor. In some embodiments, the method further includes conducting a glycerolysis reaction on the recycled transesterified product prior to introduction to the metathesis reactor. In some embodiments, the recycled transesterified product is combined with the low-weight olefin or mid-weight olefin prior to the glycerolysis reaction. In yet other embodiments, the method further includes hydrolyzing the fatty acid esters, thereby forming fatty acids.

DETAILED DESCRIPTION

Figure 1:
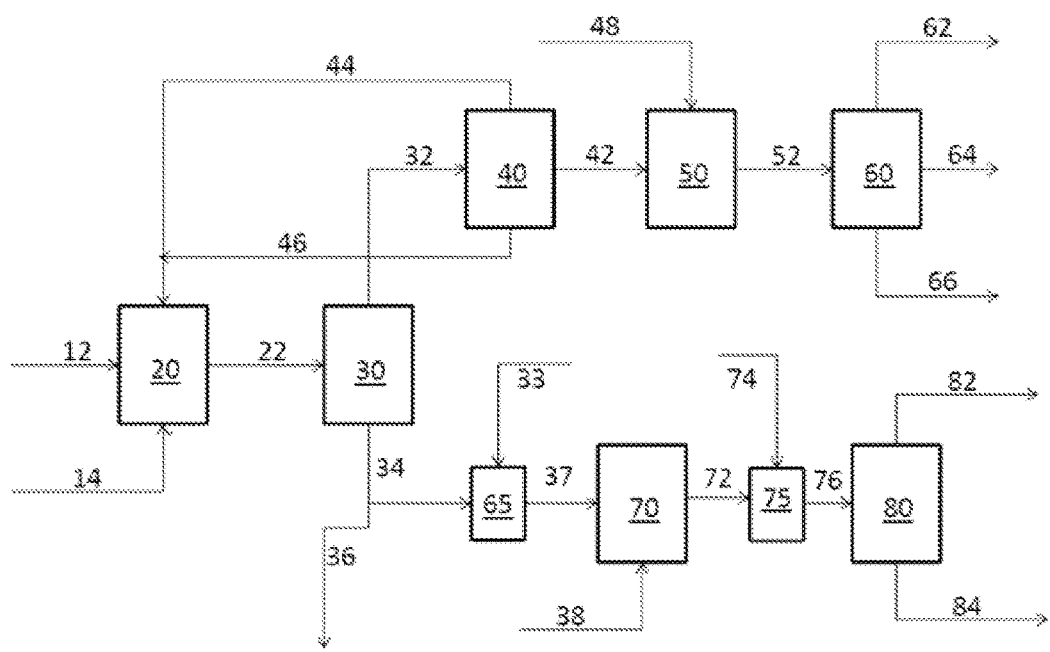
FIG. 1 depicts a schematic diagram of one embodiment of a process to produce an olefin composition and a transesterified product for further processing into high-weight esters, acids, and derivatives thereof.

The following description recites various aspects and embodiments of the inventions disclosed herein. No particular embodiment is intended to define the scope of the invention. Rather, the embodiments provide non-limiting examples of various compositions, and methods that are included within the scope of the disclosed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the term "metathesis catalyst" includes any catalyst or catalyst system that catalyzes a metathesis reaction.

As used herein, the terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include but are not limited saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (e.g., RBD soybean oil). Soybean oil may include 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, the terms "metathesize" and "metathesizing" may refer the reacting of a feedstock in the presence of a metathesis catalyst to form a "metathesized product" including a new olefinic compound. Metathesizing may refer cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer (or higher oligomer). Such triglyceride dimers may have more than one olefinic bond, thus higher oligomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: $R^a$—COO—$R^b$, wherein $R^a$ and $R^b$ denote any organic compound (such as alkyl, aryl, or silyl groups), including those bearing heteroatom containing substituent groups. In certain embodiments, $R^a$ and $R^b$ denote alkyl or aryl groups. In certain embodiments, the term "ester" or "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified. Thus, the term "unsaturated glyceride" can refer to monoglycerides, diglycerides, or triglycerides, where one or more of the acid portions of the ester contain unsaturation, e.g., a carbon-carbon double bond.

It is noted that an olefin may also include an ester, and an ester may also include an olefin, if the $R^a$ or $R^b$ group in the general formula $R^a$—COO—$R^b$ contains an unsaturated carbon-carbon double bond. For example, a "terminal olefin ester" may refer to an ester compound where $R^a$ has an olefin positioned at the end of the chain. An "internal olefin ester" may refer to an ester compound where R has an olefin positioned at an internal location on the chain. Additionally, the term "terminal olefin" may refer to an ester or an acid thereof where $R^b$ denotes hydrogen or any organic compound (such as an alkyl, aryl, or silyl group) and $R^a$ has an olefin positioned at the end of the chain, and the term "internal olefin" may refer to an ester or an acid thereof where $R^b$ denotes hydrogen or any organic compound (such as an alkyl, aryl, or silyl group) and $R^a$ has an olefin positioned at an internal location on the chain.

In certain embodiments, the ester is an "unsaturated fatty ester," which a compound that has an alkene chain with a terminal ester group. The alkene chain may be linear or branched and may optionally include one or more functional groups in addition to the ester group. For example, some unsaturated fatty esters include one or more hydroxyl groups in addition to the ester group. Unsaturated fatty esters include "unsaturated monoesters" and "unsaturated polyol esters". Unsaturated monoesters have an alkene chain that terminates in an ester group, for example, an alkyl ester group such as a methyl ester. The alkene chain of the unsaturated monoesters may include 4 to 30 carbon atoms, or 4 to 22 carbon atoms. In exemplary embodiments, the alkene chain contains 18 carbon atoms (e.g., a C18 fatty ester). The unsaturated monoesters have at least one carbon-carbon double bond in the alkene chain and may have more than one double bond in the alkene chain. In exemplary embodiments, the unsaturated fatty ester has 1 to 3 carbon-carbon double bonds in the alkene chain. In some embodiments, the unsaturated fatty esters are "unsaturated polyol esters," which refers to compounds that have at least one unsaturated fatty acid that is esterified to the hydroxyl group of a polyol. The other hydroxyl groups of the polyol may be unreacted, may be esterified with a saturated fatty acid, or may be esterified with an unsaturated fatty acid. The fatty acids in the polyol ester may be linear or branched and may optionally have functional groups other than the carboxylic acid such as one or more hydroxyl groups. Examples of polyol include glycerol, 1, 3-propanediol, 1, 2-propenediol, ethylene glycol, 1, 4-butanediol, 2, 3-butanediol, 1, 6-hexanediol, 1, 5-pentanediol, trimethylolpropane, erythritol, pentaerythritol, and sorbitol. In many embodiments, the unsaturated polyol esters are "unsaturated glycerides," which refers to a polyol ester having at least one (e.g., 1 to 3) unsaturated fatty acid that is esterified with a molecule of glycerol. The fatty acid groups may be linear or branched and may include pendant hydroxyl groups.

As used herein, the terms "extended chain ester" and "high-weight ester" may refer to ester compounds where at least a portion of the hydrocarbon chain lengths are greater than C18 (e.g., 18 carbon atoms), C18 to C100, C22 to C60, C22 to C36, C28 to C32, or C40 to C52. In certain embodiments, the high-weight ester is formed by cross-metathesizing an ester (e.g., "starting unsaturated ester" or "low-weight unsaturated ester") with an olefin feedstock, both of which may be derived from a natural oil, wherein the hydrocarbon chain of the ester is extended, and molecular weight of the ester compound is increased. In some embodiments, the cross-metathesis reaction between the starting unsaturated ester or low-weight unsaturated ester and the olefin feedstock forms a metathesized composition wherein at least a portion of the composition includes high-weight esters (e.g., at least 10 wt %, 20 wt %, 30 wt %, 40 wt %, 50 wt %, 60 wt %, 70 wt %, 80 wt %, or 90 wt % of the overall composition includes high-weight esters). Additionally, the metathesis reaction may yield self-metathesized ester products such as dibasic esters and extended chain olefins (which may also be greater than C18, C18 to C100, C22 to C60, C22 to C36, C28 to C32, or C40 to C52).

As used herein, the terms "extended chain acid" and "high-weight acid" may refer to acid compounds where at least a portion of the hydrocarbon chain lengths greater than C18, C18 to C100, C22 to C60, C22 to C36, C28 to C32, or C40 to C52. In some embodiments, the high-weight acid is formed by hydrolyzing the high-weight ester. In other embodiments, the high-weight acid is formed by cross-metathesizing an acid (e.g., "starting unsaturated acid" or "low-weight unsaturated acid") with an olefin feedstock, both of which may be derived from a natural oil, wherein the hydrocarbon chain of the acid is extended, and molecular weight of the acid compound is increased. Additionally, the metathesis reaction may yield self-metathesized acid products such as dibasic acids and extended chain olefins (which may also be greater than C18, C18 to C100, C22 to C60, C22 to C36, C28 to C32, or C40 to C52).

As used herein, the terms "extended chain derivative" and "high-weight derivative" may refer to derivative compounds of the esters, high-weight esters, acids, or high-weight acids defined above, wherein at least a portion of the hydrocarbon chain lengths in the derivative compounds are greater than C18, C18 to C100, C22 to C60, C22 to C36, C28 to C32, or C40 to C52. High-weight derivatives may refer to the compounds or mixture of compounds derived from any one or combination of methods known in the art. Such methods include, but are not limited to, saponification, fat splitting, hydrogenation (partial, selective, or full), isomerization, oxidation, and reduction. In some embodiments, the high-weight derivative is a "high-weight alcohol" or a "high-weight amide." In certain embodiments, the high-weight derivative is formed by reacting the starting unsaturated ester or low-weight ester/acid first prior to conducting a metathesis reaction to extend the hydrocarbon chain length. In other embodiments, the high-weight derivative is formed by conducting a metathesis reaction to extend the hydrocarbon chain length of the esters/acids to form a high-weight ester/acid, and then reacting the high-weight ester/acid to form its derivative.

As used herein, the terms "starting unsaturated ester" and "low-weight unsaturated esters" may refer to unsaturated ester compounds where the majority (>50 wt %) of the hydrocarbon chain length is less than or equal to C24 (e.g., 24 carbon atoms), C4 to C24, C10 to C18, C10 to C15, or C12 to C15. The low-weight unsaturated ester may include dibasic esters, including, but not limited to, 9-ODDAME (9-octadecenoic diacid methyl ester).

As used herein, the terms "starting unsaturated acid" and "low-weight unsaturated acids" may refer to unsaturated acid compounds where the majority (>50 wt %) of the hydrocarbon chain length is less than or equal to C24 (e.g., 24 carbon atoms), C4 to C24, C10 to C18, C10 to C15, or C12 to C15. The low-weight unsaturated acid may include dibasic acids, including, but not limited to, 9-ODDA (9-octadecenoic diacid).

As used herein, the terms "starting unsaturated derivative" and "low-weight derivative" may refer to unsaturated derivative compounds of the low-weight unsaturated esters and low-weight unsaturated acids defined above. In some embodiments, the low-weight derivative is a low-weight alcohol or low-weight amide.

As used herein, the term "dibasic ester" may refer to compounds having the general formula $R^a$—OOC—Y—COO—$R^b$, wherein Y, $R^a$, and $R^b$ denote any organic compound (such as alkyl, aryl, or silyl groups), including those bearing heteroatom containing substituent groups. In certain embodiments, Y is a saturated or unsaturated hydrocarbon, and $R^a$ and $R^b$ are alkyl or aryl groups. In instances where Y is a saturated hydrocarbon, the dibasic ester can be referred to as a "saturated dibasic ester." In instances where Y is an unsaturated hydrocarbon, the dibasic ester can be referred to as an "unsaturated dibasic ester."

As used herein, the term "dibasic acid" may refer to compounds having the general formula $R^a$—OOC—Y—COO—$R^b$, wherein $R^a$ and $R^b$ are hydrogen, and Y denotes any organic compound (such as an alkyl, aryl, or silyl group), including those bearing heteroatom substituent groups. In certain embodiments, Y is a saturated or unsaturated hydrocarbon. In instances where Y is a saturated hydrocarbon, the dibasic acid can be referred to as a "saturated dibasic acid." In instances where Y is an unsaturated hydrocarbon, the dibasic acid can be referred to as an "unsaturated dibasic acid."

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, the terms "olefin," "olefins," and "olefin feedstock" may refer to hydrocarbon compounds having at least one unsaturated carbon-carbon double bond. In certain embodiments, the terms "olefin," "olefins," and "olefin feedstock" may refer to a group of unsaturated carbon-carbon double bond compounds with different carbon lengths, such as "low-weight olefins," "mid-weight olefins," "high-weight olefins," or mixtures thereof. Unless noted otherwise, the term "olefin," "olefins," and "olefin feedstock" encompasses "polyunsaturated olefins" or "polyolefins" having more than one carbon-carbon double bond. It is also noted that the olefin feedstock may be sourced or purchased from a third-party, external source. In other embodiments, the olefin feedstock may be derived from a natural oil, as described in further detail below. In yet other embodiments, the olefin feedstock may be synthesized from bacteria (e.g., through fatty acid decarboxylase from *Jeotgalicoccus* species, as described in Rude et al., "Terminal Olefin (1-Alkene) Biosynthesis by a Novel P450 Fatty Acid Decarboxylase from *Jeotgalicoccus* Species," *Applied and Environmental Microbiology*, March 2011, pp. 1718-1727).

As used herein, the terms "monounsaturated olefins" and "mono-olefins" refer to hydrocarbon compounds having only one carbon-carbon double bond. A compound having a terminal carbon-carbon double bond can be referred to as an "alpha-olefin" or "terminal olefin," while an olefin having a non-terminal carbon-carbon double bond can be referred to as an "internal olefin."

In some instances, the olefin can be an "alkene," which refers to a straight- or branched-chain non-aromatic hydrocarbon carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds.

As used herein, "alpha-olefin" refers to an olefin (as defined above) that has a terminal carbon-carbon double bond. In some embodiments, the alpha-olefin a terminal alkene, which is an alkene (as defined above) having a terminal carbon-carbon double bond. Additional carbon-carbon double bonds can be present.

As used herein, "alcohol" or "alcohols" refer to compounds having the general formula: $R^a$—OH, wherein $R^a$ denotes any organic moiety (such as alkyl, aryl, or silyl groups), including those bearing heteroatom-containing substituent groups. In certain embodiments, $R^a$ denotes alkyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety.

As used herein, "alkyl" refers to a straight or branched chain saturated hydrocarbon, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number carbon atoms in an alkyl group is represented by the phrase "Cx-y alkyl," which refers to an alkyl group, as herein defined, containing from x to y, inclusive, carbon atoms. Thus, "C1-6 alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group.

As used herein, the term "low-weight olefin" may refer to any one or combination of unsaturated straight, branched, or cyclic hydrocarbons in the C2 to C14 range. Low-weight olefins include alpha-olefins. Low-weight olefins may also include polyunsaturated olefins (e.g., dienes and trienes). Low-weight olefins may also include internal olefins or "low-weight internal olefins." In certain embodiments, the low-weight internal olefin is in the C4 to C14 range. Examples of low-weight olefins in the C2 to C6 range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-weight olefins in the C7 to C9 range include 1,4-heptadiene, 1-heptene, 3,6-nonadiene, 3-nonene, 1,4,7-octatriene. Other possible low-weight olefins include styrene, vinyl cyclohexane, cardanol, limonene, and isoprene. In certain embodiments, a mixture of olefins may be used, the mixture including linear and branched low-weight olefins in the C4-C10 range. In one embodiment, a mixture of linear and branched C4 olefins may be used (e.g., combinations of: 1-butene, 2-butene, and/or isobutene). In other embodiments, a higher range of C11-C14 may be used.

As used herein, the term "mid-weight olefin" may refer to any one or combination of unsaturated straight, branched, or cyclic hydrocarbons in the C15 to C24 range. Mid-weight olefins include alpha-olefins. Mid-weight olefins may also include polyunsaturated olefins (e.g., dienes and trienes). Mid-weight olefins may also include internal olefins or "mid-weight internal olefins." In certain embodiments, a mixture of olefins may be used. In certain embodiments, the mid-weight olefin includes C15-C24 alpha olefins, C17-C21 alpha olefins, C18-C24 alpha olefins, or C20-C24 alpha olefins.

As used herein, the term "high-weight olefin" may refer to any one or combination of unsaturated straight, branched, or cyclic hydrocarbons including 25+ carbon atoms, or unsaturated hydrocarbons in the C25-C100 or C25-C36 range. High-weight olefins include alpha-olefins. High-weight olefins may also include polyunsaturated olefins (e.g., dienes and trienes). High-weight olefins may also include internal olefins or "high-weight internal olefins." In certain embodiments, a mixture of olefins may be used. In certain embodiments, the high-weight olefin includes C25+ alpha olefins, C25-C100 alpha olefins, or C25-C36 alpha olefins.

As used herein, the terms "paraffin" and "paraffins" may refer to hydrocarbon compounds having only single carbon-carbon bonds, having the general formula $C_nH_{2n+2}$, In certain embodiments, n is less than 100. In other embodiments, n is less than 70. In other embodiments, n is less than 20.

As used herein, the terms "isomerization," "isomerizes," or "isomerizing" may refer to the reaction and conversion of straight-chain hydrocarbon compounds, such as normal paraffins, into branched hydrocarbon compounds, such as iso-paraffins. In other embodiments, the isomerization of an olefin or an unsaturated ester indicates the shift of the carbon-carbon double bond to another location in the molecule (e.g., conversion from 9-decenoic acid to 8-decenoic acid), or it indicates a change in the geometry of the compound at the carbon-carbon double bond (e.g., cis to trans). As a non-limiting example, n-pentane may be isomerized into a mixture of n-pentane, 2-methylbutane, and 2,2-dimethylpropane. Isomerization of normal paraffins may be used to improve the overall properties of a fuel composition. Additionally, isomerization may refer to the conversion of branched paraffins into further, more branched paraffins.

As used herein, the term "yield" may refer to the total weight of product made from the metathesis reactions and optional hydrogenation, hydrolysis, or transesterification reactions (for example). It may also refer to the total weight of the product following a separation step and/or isomerization reaction. It may be defined in terms of a yield %, wherein the total weight of the product produced (e.g., the metathesized and, optionally, hydrolyzed and/or transesterified product) is divided by the total weight of the natural oil feedstock and olefin feedstock, if present.

As used herein, the term "diene-selective hydrogenation" or "selective hydrogenation" may refer to the targeted transformation of polyunsaturated olefins and/or esters to monounsaturated olefins and/or esters. One non-limiting example includes the selective hydrogenation of 3,6-dodecadiene to a mixture of monounsaturated products such as 1-dodecene, 2-dodecene, 3-dodecene, 4-dodecene, 5-dodecene, and/or 6-dodecene.

As used herein, the terms "conversion" and "conversion rate" may refer the conversion from polyunsaturated olefins and/or esters into saturated esters, paraffins, monounsaturated olefins, and/or monounsaturated esters. In other words, conversion=(total polyunsaturates in the feedstock−total polyunsaturates in the product)/total polyunsaturates in the feed.

As used herein, the term "selectivity" may refer to the distribution of monounsaturates formed in the hydrogenation step in comparison to paraffins and/or saturated esters. In other words, selectivity=total monounsaturates in product/(total monounsaturates in product+total saturates in the product).

As used herein, the term "wax-like composition" may refer to a composition including a high-weight ester and/or acid derived from a natural oil feedstock as described and claimed herein, wherein the properties of the natural oil derived wax composition are similar to the commercially-based wax compositions. For example, a Montan wax-like composition is derived from a natural oil feedstock and includes similar properties to Montan wax.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. Thus, such "mixtures" can be homogeneous or heterogeneous, or can be uniform or non-uniform. Further, the terms do not require the use of any particular equipment to carry out the mixing, such as an industrial mixer.

As used herein, "optionally" provides that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, providing that the group can include additional members in addition to those expressly recited. For example, the phrase, "comprises A" provides that A is present, but that other members can be present too. The terms "include," "have," and "composed of" and their grammatical variants have the same meaning. In contrast, "consist of" or "consists of" or "consisting of" refer to groups that are closed. For example, the phrase "consists of A" provides that A and only A is present.

As used herein, "or" is to be given its broadest reasonable interpretation, and is not to be limited to an either/or construction. Thus, the phrase "comprising A or B" provides that A can be present and not B, or that B is present and not A, or that A and B are both present. Further, if A, for example, defines a class that can have multiple members, e.g., $A_1$ and $A_2$, then one or more members of the class can be present concurrently.

As used herein, "providing" is to be construed as having its broadest reasonable scope. For example, providing a composition that includes a particular compound includes, but is not limited to, adding the compound to the composition, generating the compound in the composition via a chemical reaction, or receiving the composition, e.g., as the product of another process.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

A number of valuable compositions may be targeted and derived from natural oil feedstock sources. In certain embodiments, the valuable compositions include high-weight esters, high-weight acids, and/or high-weight derivative compositions of the esters/acids. These compositions may be useful as a wax, detergent, surfactant, structurants to gel organic solvents and oils, emollients, personal care products, chemicals for oil recovery, or other specialty chemicals. Additionally, in certain embodiments, the high-weight ester/acid/derivative products may be used to form wax compositions having similar properties to commercial waxes such as beeswax, Montan wax, Carnauba Wax, Candelilla Wax, or Ouricury Wax. It should be noted that there may be a desire to form "all natural" valuable compositions from natural or renewable starting materials. As described below, the starting materials may be acquired from a renewable source (e.g., a natural oil), or may be derived from a renewable source.

In certain embodiments, the high-weight esters, high-weight acids, and high-weight derivatives may be derived through the cross-metathesis reaction of a low-weight unsaturated ester, low-weight unsaturated acid, or low-weight unsaturated derivative and an olefin feedstock. In certain embodiments, the reactants (e.g., the low-weight unsaturated ester, low-weight unsaturated acid, low-weight unsaturated derivative, and/or olefin feedstock) used to form the high-weight ester/acid/derivative are purchased from external sources or derived from a separate refining unit. In other embodiments, the reactants are derived from natural oil feedstock compositions. In yet other embodiments, the olefin feedstock may be synthesized from bacteria (e.g., through fatty acid decarboxylase from *Jeotgalicoccus* species, as described in Rude et al., "Terminal Olefin (1-Alkene) Biosynthesis by a Novel P450 Fatty Acid Decarboxylase from *Jeotgalicoccus* Species," *Applied and Environmental Microbiology*, March 2011, pp. 1718-1727). These various processing options are described in greater detail below.

In some embodiments, the high-weight ester/acid/derivative compositions may be derived from a natural oil feedstock through the self-metathesis reaction of a natural oil feedstock, or the cross-metathesis reaction of the natural oil feedstock with an olefin feedstock (e.g., a low-weight olefin, mid-weight olefin, and/or high-weight olefin), in the presence of a metathesis catalyst.

In certain embodiments, prior to the metathesis reaction of the natural oil feedstock, the feedstock may be treated to render the natural oil more suitable for the subsequent metathesis reaction. In certain embodiments, the natural oil may be a vegetable oil (e.g., soybean oil) or vegetable oil derivative. The treatment of the natural oil may involve the removal of catalyst poisons, such as peroxides, which may potentially diminish the activity of the metathesis catalyst. Non-limiting examples of natural oil feedstock treatment methods to diminish catalyst poisons include those described in WO2009/020667, WO2009/023192, U.S. Patent Application Publication Nos. 2011/0160472 and 2011/0313180, and U.S. Provisional Patent Application Nos. 61/783,720 and 61/784,321, herein incorporated by reference in their entireties.

Additionally, in certain embodiments, the olefin feedstock may also be treated, in combination with or separately from the natural oil feedstock, prior to the metathesis reaction. Like the natural oil treatment, the olefin feedstock may be treated to remove poisons that may impact or diminish catalyst activity using any of the above-mentioned methods of treatment.

In certain embodiments, the olefin feedstock may be self-metathesized to form a metathesized olefin (e.g., a metathesized low-weight olefin, metathesized mid-weight olefin, or metathesized high-weight olefin) in order to adjust the properties of the olefin and the potential products following metathesis with the natural oil. In some embodiments, the olefin feedstock is self-metathesized in the presence of a rhenium oxide catalyst (e.g., rhenium oxide supported on alumina) or tungsten oxide catalyst (e.g., tungsten oxide supported on silica). This reaction may be conducted in a fixed bed reactor. In one embodiment, the olefin feedstock is 1-butene. The 1-butene may be self-metathesized over rhenium oxide catalyst in a fixed bed reactor to produce mainly 3-hexene and ethylene. Ethylene may be separated from the reactor effluent for further processing, such as being sent to an ethylene purification system or ethylene oxide system. Unreacted olefin feedstock (e.g., 1-butene) may be recycled to the fixed bed reactor and the metathesized olefin feedstock (e.g., 3-hexene) may be sent to the metathesis reactor for metathesis with the natural oil.

In other embodiments, the olefin feedstock is isomerized prior to being metathesized with the natural oil. Adjusting the composition and properties of the olefin feedstock through isomerization may allow for different products or different ratios of products to be formed following metathesis of the olefin feedstock (e.g., low-weight olefin, mid-weight olefin, and/or high-weight olefin) with a natural oil. By using branched low-weight olefins, branched mid-weight olefins, or branched high-weight olefins in the metathesis reaction, the metathesized product will include branched olefins, which can be subsequently hydrogenated to isoparaffins. In certain embodiments, the branched olefins may help achieve the desired performance/sensory properties for a personal care application. In certain embodiments, C11-C14 olefins may be targeted following metathesis and separation steps through isomerization of the low-weight olefin. In other embodiments, the branched olefins may help target longer chain esters for use as detergents or cleaning compositions. In some embodiments, C10-C15 or C11-C14 methyl esters may be targeted following metathesis, separation, and transesterification steps (discussed in detail below). Isomerization reactions are well-known in the art, as described in U.S. Pat. Nos. 3,150,205; 4,210,771; 5,095,169; and 6,214,764, herein incorporated by reference in their entireties.

In certain embodiments, the olefin feedstock 14 is provided or purchased from an external, third-party source. In other embodiments, the olefin feedstock 14 is derived from a natural oil feedstock (e.g., the olefin feedstock is derived or produced from a renewable source). In some embodiments, as discussed below, the olefin feedstock 14 is derived from olefins produced downstream of the metathesis reaction and separation process. In yet other embodiments, the olefin feedstock 14 may be synthesized from bacteria (e.g., through fatty acid decarboxylase from *Jeotgalicoccus* species, as described in Rude et al., "Terminal Olefin (1-Alkene) Biosynthesis by a Novel P450 Fatty Acid Decarboxylase from *Jeotgalicoccus* Species," *Applied and Environmental Microbiology*, March 2011, pp. 1718-1727). In certain embodiments, the olefin feedstock may be made from: (1) naturally occurring materials such as fatty alcohols, which are then dehydrated, (2) biological processes that selectively produce olefins from naturally occurring saturated hydrocarbon compounds, or (3) deriving ethanol from a natural source such as corn, and dehydrating the ethanol to form ethylene, and then oligomerizing the ethylene to form the olefin feedstock.

In one example, the olefin feedstock 33 (e.g., a mixture of C12-C18 olefins) may be derived from fatty acid esters (e.g., C12-C18 fatty acid methyl esters). The fatty acid esters may have been formed by transesterifying a natural oil with an alkanol (e.g., methanol). The fatty acid esters (e.g., fatty acid methyl esters such as methyl palmitate or methyl stearate) are then reduced to form a terminal alcohol (e.g., terminal C16 and C18 alcohols). The terminal alcohols are then catalytically dehydrated to form olefins (e.g., C16 and C18 olefins). In certain embodiments, the catalytically dehydration reaction can lead to high alpha-olefin production (e.g., >98%).

As depicted in FIG. 1, after the optional treatment of the natural oil feedstock and/or olefin feedstock, the natural oil 12 is reacted with itself, or combined with an olefin feedstock 14 in a metathesis reactor 20 in the presence of a metathesis catalyst. Metathesis catalysts and metathesis reaction conditions are discussed in greater detail below. In certain embodiments, in the presence of a metathesis catalyst, the natural oil 12 undergoes a self-metathesis reaction with itself. In other embodiments, in the presence of the metathesis catalyst, the natural oil 12 undergoes a cross-metathesis reaction with the olefin feedstock 14. In certain embodiments, the natural oil 12 undergoes both self- and cross-metathesis reactions in parallel metathesis reactors. The self-metathesis and/or cross-metathesis reaction form a metathesized product 22 wherein the metathesized product 22 includes olefins 32 and esters 34 (e.g., triglycerides with extended chain esters). It should also be noted that depending on the experimental conditions used, the olefins and esters within the metathesized product may also undergo self-metathesis during this process, and thus can result in various mixtures of products (including extended chain esters or other derivatives). It should also be noted that any downstream products formed from the olefins 32 and esters 34 may be used together, or may be separated for alternative uses.

In certain embodiments, the olefin feedstock 14 includes low-weight olefins in the C2 to C6 range. In another embodiment, the olefin feedstock 14 includes at least one alpha-olefin in the C2 to C10 range. In another embodiment, the olefin feedstock 14 includes at least one branched low-weight olefin in the C4 to C10 range.

In certain embodiments, the olefin feedstock 14 includes mid-weight olefins having unsaturated straight, branched, or cyclic hydrocarbons in the C15 to C24 range. In some embodiments, the mid-weight olefin is an alpha-olefin. In some embodiments, the mid-weight olefin is an alpha-olefin selected from the group including 1-pentadecene, 1-hexadecene, 1-heptadecene, 1-octadecene, 1-nonadecene, 1-icosene, 1-henicosene, 1-tricosene, 1-tetracosene, and combinations thereof. In one particular embodiment, the mid-weight olefin is 1-octadecene. In other embodiments, the mid-weight olefin includes a mixture of C15-C24 alpha olefins, C17-C21 alpha olefins, C18-C24 alpha olefins, or C20-C24 alpha olefins.

In certain embodiments, the olefin feedstock 14 includes high-weight olefins having unsaturated straight, branched, or cyclic hydrocarbons in the C25+, C25-C100, or C25-C36 range. In some embodiments, the high-weight olefin is an alpha-olefin. In some embodiments, the high-weight olefin is an alpha-olefin selected from the group including 1-pentacosene, 1-hexacosene, 1-heptacosene, 1-octacosene, 1-nonacosene, 1-triacontene, 1-hentriacontene, 1-dotriacontene, 1-tritriacontene, 1-tetratricontene, 1-pentatriacontene, 1-hexatriacontene, and combinations thereof.

It is possible to use a mixture of low-, mid-, or high-weight olefins in the reaction to achieve the desired metathesis product distribution. In certain embodiments, the olefin feedstock 14 includes a mixture of C14-C36 olefins, C16-C26 olefins, or C20-C24 olefins. In one embodiment, the olefin feedstock 14 includes a mixture of C14-C36 alpha-olefins. In another embodiment, the olefin feedstock 14 includes a mixture of C16-C26 alpha-olefins or C20-C24 alpha-olefins.

As noted, it is possible to use a mixture of various linear or branched olefins in the reaction to achieve the desired metathesis product distribution. In certain embodiments, the mixture includes linear and/or branched low-weight olefins. In other embodiments, the mixture includes linear and/or branched mid-weight olefins. In other embodiments, the mixture includes linear and/or branched high-weight olefins.

In one embodiment, a mixture of butenes (1-butene, 2-butenes, and, optionally, isobutene) may be employed as the low-weight olefin, offering a low cost, commercially available feedstock instead a purified source of one particular butene. Such low cost mixed butene feedstocks may be diluted with n-butane and/or isobutane.

In certain embodiments, recycled streams from downstream separation units may be introduced to the metathesis reactor 20 in addition to the natural oil 12 and, in some embodiments, the olefin feedstock 14. For instance, a C2-C6 recycle olefin stream or a C3-C4 bottoms stream from an overhead separation unit may be returned to the metathesis reactor. As depicted in FIG. 1, a light weight olefin stream 44 from an olefin separation unit 40 may be returned to the metathesis reactor 20. In another embodiment, the C3-C4 bottoms stream and the light weight olefin stream 44 are combined together and returned to the metathesis reactor 20. In another embodiment, a C15+ bottoms stream 46 from the olefin separation unit 40 is returned to the metathesis reactor 20. In another embodiment, all of the aforementioned recycle streams are returned to the metathesis reactor 20. In another embodiment, one or more of the recycle streams may be selectively hydrogenated to increase the concentration of mono-olefins in the stream.

In other embodiments, various ester or acid streams downstream of the metathesis/separation, hydrolysis, or transesterification reactions/units may also be recycled or returned to the metathesis reactor 20. In certain embodiments, a glycerolysis reaction may be conducted on the recycled ester stream to prevent or limit the amount of free glycerol entering the metathesis reactor 20. In some embodiments, the recycled ester stream will undergo a purification step to limit the amount of methanol being recycled to the metathesis reactor 20. In certain embodiments, low-weight esters/acids may be separated from the high-weight ester/acids and recycled back to the metathesis reactor 20 to improve the overall yield of the targeted high-weight ester/acid products.

In some embodiments, the recycled ester stream is combined with the olefin feedstock 14 prior to conducting the glycerolysis reaction and entering the metathesis reactor 20. The glycerolysis reaction may also limit or prevent free fatty acid methyl esters from entering the metathesis reaction and subsequently exiting the metathesis reactor as free fatty acid methyl esters that may boil close to various high-valued olefin products. In such cases, these methyl ester components may be separated with the olefins during the separation of the olefins and esters. Such methyl ester components may be difficult to separate from the olefins by distillation. In another embodiment, the recycled ester or acid stream may be partially or selectively hydrogenated to increase the concentration of monounsaturated esters or acids in the stream.

The metathesis reaction in the metathesis reactor 20 produces a metathesized product 22. In one embodiment, the metathesized product 22 enters a flash vessel operated under temperature and pressure conditions which cause C2 or C2-C3 compounds to flash off and be removed overhead. The C2 or C2-C3 light ends include a majority of hydrocarbon compounds having a carbon number of 2 or 3. In certain embodiments, the C2 or C2-C3 light ends are then sent to an overhead separation unit, wherein the C2 or C2-C3 compounds are further separated overhead from the heavier compounds that flashed off with the C2-C3 compounds. These heavier compounds may be C3-C5 compounds carried overhead with the C2 or C2-C3 compounds. After separation in the overhead separation unit, the overhead C2 or C2-C3 stream may then be used as a fuel source. These hydrocarbons have their own value outside the scope of a fuel composition, and may be used or separated at this stage for other valued compositions and applications. In certain embodiments, the bottoms stream from the overhead separation unit containing mostly C3-C5 compounds is returned as a recycle stream to the metathesis reactor. In the flash vessel, the metathesized product 22 that does not flash overhead is sent downstream for separation in a separation unit 30, such as a distillation column.

Prior to the separation unit 30, in certain embodiments, the metathesized product 22 may be contacted with a reactant or reagent to deactivate or to extract the catalyst. Reactants/reagents and methods of deactivation are described in U.S. Patent Application Publication Nos. 2011/0113679 and 2013/0085288, both of which are herein incorporated by reference in their entireties.

Additionally, in certain embodiments, prior to the separation unit 30 (and after catalyst separation, in some instances), the metathesis product 22 may be sent to a hydrogenation unit, wherein the carbon-carbon double bonds in the olefins and esters are partially, selectively, or fully saturated with hydrogen gas. Hydrogenation may be conducted according to any known method in the art for hydrogenating double bond-containing compounds such as the olefins and esters present in the metathesis product 22. In certain embodiments, the metathesis product is partially or selectively hydrogenated to increase the concentration of monounsaturated olefins and/or ester compounds present in the metathesis product 22. In certain embodiments, in the diene selective hydrogenation, the conversion rate from the polyunsaturated olefins and esters to paraffins, saturated esters, monounsaturated olefins, and monounsaturated esters may be at least 50%, at least 75%, at least 85%, at least 95%, or at least 98%. The selectivity towards the monounsaturated olefins and monounsaturated esters instead of the paraffins and saturated esters is at least 90%, at least 95%, at least 99%, or at least 99.5%.

In certain embodiments, in the hydrogenation unit, hydrogen gas is reacted with the metathesis product 22 in the presence of a hydrogenation catalyst to produce a hydrogenated product including partially to fully hydrogenated paraffins/olefins and partially to fully hydrogenated esters. In some embodiments, the metathesis product 22 is hydrogenated in the presence of a hydrogenation catalyst including nickel, copper, palladium, platinum, molybdenum, iron, ruthenium, osmium, rhodium, or iridium, individually or in combinations thereof. Useful catalysts may be heterogeneous or homogeneous. In some embodiments, the catalysts are supported nickel or sponge nickel type catalysts. Hydrogenation catalysts and methods of hydrogenation are described in U.S. Patent Application Publication No. 2011/0113679 and 2013/0085288, both of which are herein incorporated by reference in their entireties.

In the separation unit 30, in certain embodiments, the metathesized product 22 (from a hydrogenation unit, metathesis reactor 20, or catalyst separation unit) is separated into at least two product streams. In one embodiment, the metathesized product 22 is sent to the separation unit 30, or distillation column, to separate the olefins 32 from the esters 34. In other embodiments, the separation unit 30 is an adsorptive separation unit (e.g., simulated moving bed chromatography), solvent extraction unit, or fractional crystallization unit. In another embodiment, a byproduct stream including C7's and cyclohexadienes (e.g., 1,4-cyclohexadiene) may be removed in a side-stream from the separation unit 30. In certain embodiments, the separated olefins 32 may include hydrocarbons with carbon numbers up to 24, up to 30, up to 36, up to 42, up to 48, or up to 100. In certain embodiments, the esters 34 may include metathesized glycerides. In other words, the lighter end olefins 32 may be separated or distilled overhead for processing into olefin compositions, while the esters 34, including mostly compounds having carboxylic acid/ester functionality, are drawn into a bottoms stream. Based on the quality of the separation, it is possible for some ester compounds to be carried into the overhead olefin stream 32, and it is also possible for some heavier olefin hydrocarbons to be carried into the ester stream 34. Additionally, the separated cyclohexadienes (e.g., 1,4-cyclohexadiene) may be dehydrogenated to form benzene, or isomerized to produce 1,3-cyclohexadiene. Examples of catalytic dehydrogenation catalysts include platinum supported on alumina. Examples of oxidative dehydrogenation catalysts include mixed metal oxides such as molybdenum, vanadium, niobium, tellurium, magnesium, and/or aluminum. Other dehydrogenation catalysts examples include cerium/zirconium, alkaline earth/nickel, calcium-nickel-phosphate, chromium, iron-chromium oxide, bismuth/molybdenum, tin/antimony, silver, or copper.

In one embodiment, the olefins 32 may be collected and sold for any number of known uses. In other embodiments, the olefins 32 are further processed in an olefin separation unit 40 and/or hydrogenation unit 50 (where the olefinic bonds are saturated with hydrogen gas 48, as described below). In other embodiments, the olefins 32 are selectively hydrogenated to increase the mono-olefin concentration. In other embodiments, the resulting olefins are separated and recycled back into the reactor to serve as feedstock for further metathesis. In other embodiments, esters 34 including heavier end glycerides and free fatty acids are separated or distilled as a bottoms product for further processing into various products. In certain embodiments, further processing may target the production of the following non-limiting examples: fatty acid methyl esters; biodiesel; 9DA esters, 9UDA esters, and/or 9DDA esters; 9DA, 9UDA, and/or 9DDA; alkali metal salts and alkaline earth metal salts of 9DA, 9UDA, and/or 9DDA; diacids, and/or diesters of the transesterified products; and mixtures thereof. In certain embodiments, further processing may target the production of C15-C18 fatty acids and/or esters. In other embodiments, further processing may target the production of diacids and/or diesters. In yet other embodiments, further processing may target the production of compounds having molecular weights greater than the molecular weights of stearic acid and/or linolenic acid (e.g., high-weight esters or high-weight acids). In some embodiments, the heavier end esters (C18+ and diesters) from the bottoms product are capable of being used to form a high-weight ester or high-weight acid. The bottoms product may be cross- or self-metathesized to extend the chain length of the ester. The bottoms product, or metathesized bottoms product, may undergo further processing to form a derivative of the high-weight ester, such as hydrolysis to form a high-weight acid.

As depicted in FIG. 1, regarding the overhead olefins 32 from the separation unit 30, the olefins 32 may be further separated or distilled in the olefin separation unit 40 to separate the various compositions. The olefin separation unit 40 may include a number of distillation towers. In some embodiments, the various composition streams are separated using at least four distillation towers. In other embodiments, three towers or less are used to separate the olefin compositions.

In one embodiment, light end olefins 44 including C2-C9 compounds may be distilled into an overhead stream from the olefin separation unit 40. In certain embodiments, the light end olefins 44 include a majority of C3-C8 hydrocarbon compounds. The light end olefins 44 may be recycled to the metathesis reactor 20, purged from the system for further processing and sold, or a combination of the two. In one embodiment, the light end olefins 44 may be partially purged from the system and partially recycled to the metathesis reactor 20. With regards to the other streams in the olefin separation unit 40, a heavier C16+, C18+, C20+, C22+, or C24+ compound stream may be separated out as an olefin bottoms stream 46. This olefin bottoms stream 46 may be purged or recycled to the metathesis reactor 20 for further processing, or a combination of the two. In another embodiment, a center-cut olefin stream 42 may be separated out of the olefin distillation unit for further processing.

In other embodiments, the olefins 32, light end olefins 44, or center-cut olefins 42 may be self-metathesized in the presence of a metathesis catalyst in a secondary metathesis reactor in order to produce heavier weight olefin products (e.g., C14+, C16+, C18+, C18 to C100, C22 to C60, C22 to C36, C28 to C32, or C40 to C52). In one embodiment, the metathesis catalyst is a rhenium oxide catalyst (e.g., rhenium oxide supported on alumina). In another embodiment, the metathesis is a tungsten oxide catalyst (e.g., tungsten oxide supported on silica). This metathesis reaction may be conducted in a fixed bed reactor. The heavier weight olefins may be used as surfactants or oil lubes, or hydrogenated for use as a wax, structurant, or emollient. In some embodiments, the lighter olefin byproducts from the self-metathesis reaction may be recycled back to the secondary metathesis reactor or primary metathesis reactor 20 for further processing.

In other embodiments, a selected portion of the olefins 32 may be used as a cross-metathesis reactant with a selected portion of the esters 34 or transesterified product 72 to produce high-weight ester products or derivatives thereof, as well as olefin byproducts. In some embodiments, the olefin bottoms 46 or the heavier weight olefins may be used for the cross-metathesis reactant with the esters 34 or transesterified product 72.

In certain embodiments, the olefins 32, center-cut olefins 42, light end olefins 44, or olefin bottoms 46 may be pre-treated to remove potential catalyst poisons prior to the hydrogenation unit 50. Examples of potential feedstock pretreatments (such as adsorbants, alumina, or heat) for the olefin stream(s) are described above with regard to potential treatment of the natural oil 12.

As mentioned, in one embodiment, the olefins 32 from the separation unit 30 may be sent directly to the hydrogenation unit 50. In another embodiment, the center-cut olefins 42, light end olefins 44, or olefin bottoms 46 from the olefin separation unit 40 may be sent to the hydrogenation unit 50. Hydrogenation may be conducted according to any known method in the art for hydrogenating double bond-containing compounds such as the olefins 32, center-cut olefins 42, light end olefins 44, or olefin bottoms 46. In certain embodiments, in the hydrogenation unit 50, hydrogen gas 48 is reacted with the olefins 32, center-cut olefins 42, light end olefins 44, or olefin bottoms 46 in the presence of a hydrogenation catalyst to produce a hydrogenated product 52. Hydrogenation catalysts and reaction conditions are discussed above. During hydrogenation, the carbon-carbon double bond containing compounds in the olefins are hydrogenated to partially, selectively, or fully saturated compounds by the hydrogen gas 48.

In certain embodiments, the hydrogenated product 52 may include hydrocarbons with a distribution that is centered at a hydrocarbon value greater than C18, C18 to C100, C22 to C60, C22 to C36, C28 to C32, or C40 to C52. Such hydrogenated products may be used in personal care products, chemicals for oil recovery, Fischer-Tropsch waxes, or polyethylene wax replacements, for example.

In other embodiments, the olefins are selectively hydrogenated to decrease the presence of polyunsaturated olefins and increase the presence of monounsaturated olefins. The olefins 32 from the separation unit 30 may include polyolefins (e.g., dienes or trienes), with the amount of polyunsaturation depending on the inherent characteristics of the natural oil 12. Polyunsaturated olefins, such as dienes and trienes, may pose a number of problems for downstream processing and end-use over monounsaturated olefin compounds. Dienes and trienes may have oxidation rates that are 10-100 times those of monounsaturated olefins. These oxidation products would make some materials unsuitable for some applications such as advanced oilfield recovery. It therefore may prove beneficial to reduce the amount of polyunsaturation present in the olefins 32 from the separation unit 30. At the same time, olefins may be more valuable that paraffin compositions. Therefore, in some embodiments, the olefins 32, light end olefins 44, center-cut olefins 42, or olefin bottoms 46 are partially or selectively hydrogenated to remove the polyunsaturation and form monounsaturated olefins. Certain reaction conditions, such as temperature, pressure, time of reaction, and hydrogenation catalyst type, are described above with regard to partial or selective hydrogenation of the metathesis product 22.

Partially or selectively hydrogenated olefin products 52 may be useful for the preparation of surfactants/surfactant precursors including but not limited to linear alkyl benzene. In certain embodiments, the partially or the selectively hydrogenated product 52 may be useful for but not limited to advanced oilfield recovery or drilling fluids.

In certain embodiments, in the diene selective hydrogenation, the conversion rate from polyunsaturated olefins to paraffins and monounsaturated olefins may be at least 50%, at least 75%, at least 85%, at least 95%, or at least 98%. The selectivity towards monounsaturated olefins instead of paraffin is at least 90%, at least 95%, at least 99%, or at least 99.5%.

In certain embodiments, after full, partial, or selective hydrogenation, the hydrogenation catalyst may be removed from the hydrogenated product 52 using known techniques in the art, for example, by filtration, or methods described in U.S. Patent Application Publication No. 2011/0113679 and 2013/0085288.

In certain embodiments, based upon the quality of the hydrogenated product 52 produced in the hydrogenation unit 50, the olefin hydrogenated product 52 may be isomerized to assist in targeting of desired product properties such as flash point, freeze point, energy density, cetane number, or end point distillation temperature, among other parameters (such as sensory properties for personal care applications). Isomerization reactions are well-known in the art, as described in U.S. Pat. Nos. 3,150,205; 4,210,771; 5,095, 169; and 6,214,764, herein incorporated by reference in their entireties.

In certain embodiments, the isomerization may occur concurrently with the hydrogenation step in the hydrogenation unit 50, thereby targeting a desired product. In other embodiments, the isomerization step may occur before the hydrogenation step (e.g., the olefins 32 or center-cut olefins 42 may be isomerized before the hydrogenation unit 50). In yet other embodiments, it is possible that the isomerization step may be avoided or reduced in scope based upon the selection of low-weight olefins, mid-weight olefins, and/or high-weight olefins within the olefin feedstock 14 for the metathesis reaction.

As depicted in FIG. 1, the hydrogenated product 52 may be further processed in a separation unit 60, removing any remaining byproducts from the hydrogenated product 52, such as hydrogen gas, water, light end C2-C9 hydrocarbons, or C15+ hydrocarbons, thereby producing a targeted composition. The separation unit 60 may include a number of distillation towers. In some embodiments, the various composition streams are separated using at least four distillation towers. In other embodiments, three towers or less are used.

In one embodiment, the hydrogenated product 52 may be separated into various product cuts, such as a C9-C15 product 64, a light-ends C2-C9 fraction 62, and/or a C15+ heavy-ends fraction 66. Distillation may be used to separate the fractions.

With regard to the esters 34 from the distillation unit 30 (e.g., triglycerides with extended chain esters), in certain embodiments, the esters 34 may be entirely withdrawn as an ester product stream 36 and processed further or sold for its own value, as depicted in FIG. 1. As a non-limiting example, the esters 34 may include various triglycerides with extended chain esters that may be used within a wax, detergent, surfactant, structurant, emollient, chemicals for oil recovery, or personal care product. In certain embodiments, based on the olefin feedstock 14 used in the metathesis reaction, the esters 34 may include high-weight esters (and/or diesters from self-metathesis). Based upon the quality of separation between olefins and esters, the esters 34 may include some heavier olefin components carried with the triglycerides. In other embodiments, the esters 34 may be further processed in a biorefinery or another chemical or fuel processing unit known in the art, thereby producing various products such as biodiesel, waxes, detergents, surfactants, structurants, emollients, personal care compositions, chemicals for oil recovery, or other specialty chemicals that have higher value than that of the triglycerides, for example. Various ester processing steps are described in greater detail below, with reference to FIGS. 1-3. Alternatively, in certain embodiments, the esters 34 may be partially withdrawn from the system and sold, with the remainder further processed in the biorefinery or another chemical or fuel processing unit.

Figure 2:
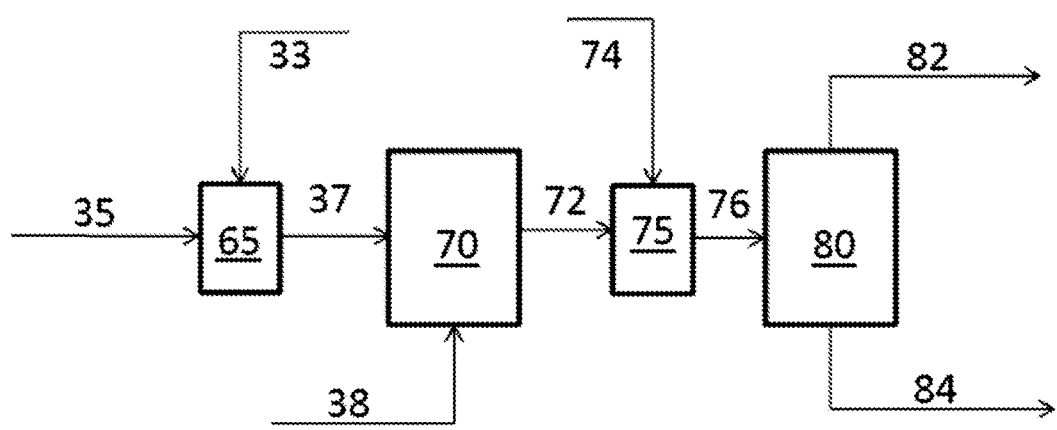
FIG. 2 depicts a schematic diagram of one embodiment of a process to produce a high-weight ester composition from the cross-metathesis reaction of an olefin feedstock and a starting unsaturated ester/acid/derivative.

In other embodiments, as depicted in FIG. 2, a feedstock including low-weight unsaturated esters/acids/derivatives 35 is not necessarily derived from a distillation unit, as in FIG. 1. The low-weight unsaturated esters/acids/derivatives 35 may be purchased from an external source or derived in an alternative method from that depicted in FIG. 1. The low-weight unsaturated esters/acids/derivatives 35 may be selected from the group including fatty acid esters, monoacylglycerides, diacylglyceridies, triacylglycerides, other polyfunctional esters (e.g., dimers, trimers, tetramers), acids, and derivatives thereof, and mixtures thereof. In certain embodiments, the low-weight unsaturated esters/acids/derivatives 35 have hydrocarbon chain lengths less than or equal to C24, C4 to C24, C10 to C18, C10 to C15, or C12 to C15. The hydrocarbon chain length may include an unsaturated carbon-carbon bond at the C9 position, but other starting materials may have different chain lengths or unsaturated carbon-carbon bond locations, depending on the source.

In some embodiments, the esters 34 (FIG. 1) or the low-weight unsaturated esters/acids/derivatives 35 (FIG. 2) may be pre-treated to remove potential catalyst poisons prior to further processing. Examples of potential feedstock pre-treatments (such as adsorbants, alumina, or heat) for the esters 34 or the low-weight unsaturated esters/acids/derivatives 35 are described above with regard to potential treatment of the natural oil 12.

In certain embodiments, the esters 34 or the low-weight unsaturated esters 35 may be selectively hydrogenated to decrease the presence of polyunsaturated esters and increase the presence of monounsaturated esters. Certain reaction conditions, such as temperature, pressure, time of reaction, and hydrogenation catalyst type, are described above with regard to selective hydrogenation of the metathesis product 22. In certain embodiments, in the diene selective hydrogenation, the conversion rate from polyunsaturated esters to saturated and monounsaturated esters may be at least 50%, at least 75%, at least 85%, at least 95%, or at least 98%. The selectivity towards monounsaturated esters instead of saturated esters is at least 90%, at least 95%, at least 99%, or at least 99.5%.

Prior to or following a metathesis reaction (described below), the esters 34 or the low-weight unsaturated esters 35 may undergo a hydrolysis reaction with water to form an acid or low-weight unsaturated acid. Following hydrolysis, in some embodiments, the product stream may be sent to a flash column or decanter to remove methanol and water from the acid. Additionally, prior to or following a metathesis reaction, the low-weight unsaturated esters or low-weight unsaturated acids may be reacted to form a low-weight unsaturated derivative (e.g., a low-weight unsaturated alcohol, low-weight unsaturated amide composition, or low-weight selectively hydrogenated ester).

As depicted in FIGS. 1 and 2, the esters 34 or the low-weight unsaturated esters 35 (or derivatives thereof) may be cross-metathesized with an olefin feedstock 33 in a metathesis reactor 65 in the presence of a metathesis catalyst, with the intent of extending the hydrocarbon chain lengths to form extended chain esters or high-weight esters/acids/derivatives 37. The olefin feedstock 33 may be selected from the group including low-weight olefins, mid-weight olefins, high-weight olefins, and combinations thereof.

In certain embodiments, the olefin feedstock 33 is provided or purchased from an external, third-party source. In other embodiments, the olefin feedstock 33 is derived from a natural oil feedstock (e.g., the olefin feedstock is derived or produced from a renewable source). In yet other embodiments, the olefin feedstock 33 may be synthesized from bacteria (e.g., through fatty acid decarboxylase from *Jeotgalicoccus* species, as described in Rude et al., "Terminal Olefin (1-Alkene) Biosynthesis by a Novel P450 Fatty Acid Decarboxylase from *Jeotgalicoccus* Species," *Applied and Environmental Microbiology*, March 2011, pp. 1718-1727). In certain embodiments, the olefin feedstock 33 may be made from: (1) naturally occurring materials such as fatty alcohols, which are then dehydrated, (2) biological processes that selectively produce olefins from naturally occurring saturated hydrocarbon compounds, or (3) deriving ethanol from a natural source such as corn, and dehydrating the ethanol to form ethylene, and then oligomerizing the ethylene to form the olefin feedstock.

In some embodiments, as noted above, the olefin feedstock 33 is derived from the olefins 32 from the separation unit 30 or a downstream unit of the separation unit. In some embodiments, the olefin bottoms or heavier weight olefin products (e.g., C14+, C16+, C18+, C16-C100, C16-C26, C20-C24, C22-C60, C24-C36, C28-C32, or C40-C52 olefins) may be used as the olefin feedstock 33 for the cross-metathesis reactant with the esters 34.

In one example, the olefin feedstock 33 (e.g., a mixture of C12-C18 olefins) may be derived from fatty acid esters (e.g., C12-C18 fatty acid methyl esters). The fatty acid esters may have been formed by transesterifying a natural oil with an alkanol (e.g., methanol). The fatty acid esters (e.g., fatty acid methyl esters such as methyl palmitate or methyl stearate) are then reduced to form a terminal alcohol (e.g., terminal C16 and C18 alcohols). The terminal alcohols are then catalytically dehydrated to form olefins (e.g., C16 and C18 olefins). In certain embodiments, the catalytically dehydration reaction can lead to high alpha-olefin production (e.g., >98%).

In certain embodiments, the esters 34 or the low-weight unsaturated esters/acids/derivatives 35 are cross-metathesized with a low-weight olefin in a metathesis reactor 65. In some embodiments, the low-weight olefin includes unsaturated straight, branched, or cyclic hydrocarbons in the C2 to C14 range, C4 to C10 range, or C11 to C14 range. In some embodiments, the low-weight olefin is an alpha-olefin.

In certain embodiments, the esters 34 or the low-weight unsaturated esters/acids/derivatives 35 are cross-metathesized with a mid-weight olefin in a metathesis reactor 65. In some embodiments, the mid-weight olefin includes unsaturated straight, branched, or cyclic hydrocarbons in the C15 to C24 range. In some embodiments, the mid-weight olefin is an alpha-olefin. In some embodiments, the mid-weight olefin is an alpha-olefin selected from the group including 1-pentadecene, 1-hexadecene, 1-heptadecene, 1-octadecene, 1-nonadecene, 1-icosene, 1-henicosene, 1-tricosene, 1-tetracosene, and combinations thereof. In one particular embodiment, the mid-weight olefin is 1-octadecene. In other embodiments, the mid-weight olefin includes a mixture of C15-C24 alpha olefins, C17-C21 alpha olefins, C18-C24 alpha olefins, or C20-C24 alpha olefins. In one particular example, the esters 34 or the low-weight unsaturated esters/acids/derivatives 35 are cross-metathesized with a C20-C24 alpha-olefin.

In other embodiments, the esters 34 or the low-weight unsaturated esters/acids/derivatives 35 are cross-metathesized with a high-weight olefin in a metathesis reactor 65. In some embodiments, the high-weight olefin includes unsaturated straight, branched, or cyclic hydrocarbons in the C25+, C25-C100, or C25-C36 range. In some embodiments, the high-weight olefin is an alpha-olefin. In some embodiments, the high-weight olefin is an alpha-olefin selected from the group including 1-pentacosene, 1-hexacosene, 1-heptacosene, 1-octacosene, 1-nonacosene, 1-triacontene, 1-hentriacontene, 1-dotriacontene, 1-tritriacontene, 1-tetratricontene, 1-pentatriacontene, 1-hexatriacontene, and combinations thereof.

In certain embodiments, the esters 34, the low-weight unsaturated esters 35 or the high-weight esters 37 (which have been selectively hydrogenated in some embodiments) are sent to a transesterification unit 70. Within the transesterification unit 70, the esters 34, the low-weight unsaturated esters 35, or the high-weight esters 37 may be reacted with at least one alcohol 38 in the presence of a transesterification catalyst. In certain embodiments, the alcohol includes an alkanol, such as methanol and/or ethanol. In another embodiment, the alcohol 38 includes glycerol (and the transesterification reaction is a glycerolysis reaction). In another embodiment, the alcohol includes a C16-C18 alcohol.

To the extent the esters 34, low-weight unsaturated esters 35, or the high-weight esters 37 have previously been hydrolyzed to form an acid composition, the acid composition may be reacted with a fatty acid ester in the presence of a transesterification catalyst. In some embodiments, the fatty acid ester is a fatty acid methyl ester. In one particular embodiment, the fatty acid ester is a C16-C18 fatty acid methyl ester (e.g., derived from a natural oil feedstock).

The transesterification reaction may be conducted at any temperature or pressure, (e.g., 60-70° C. and 1 atm). In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters.

In certain embodiments, the transesterification reaction may produce a transesterified product 72 including monomer terminal olefin esters or acids having the following structure:

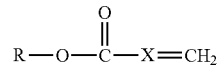

where X is a C3-C98 saturated or unsaturated alkyl chain, and R is an alkyl group. In some embodiments, R is methyl. In other embodiments, R is —OH.

In certain embodiments, the transesterification reaction may produce transesterified products 72 including saturated and/or unsaturated monomer fatty acid methyl esters ("FAME"), glycerin, methanol, and/or free fatty acids. In some embodiments, the high-weight ester derived from the transesterified product 72 may further undergo a hydrolysis reaction with water to form a high-weight acid. Following hydrolysis, in some embodiments, the product stream may be sent to a flash column or decanter to remove methanol and water from the high-weight acid.

In certain embodiments, where the transesterification reaction involves a high-weight ester/acid/derivative, the transesterified products 72, or fraction thereof, includes a source for personal care products, structurants, emollients, lubricants, waxes, films, paints, paint strippers, coatings, plasticizers, resins, binders, solvents, polyols, soil stabilization, chemical grouting, chemicals for oil recovery, oilfield drilling fluids, crop protection products, surfactants, intermediates, and adhesives. In some embodiments, the high-weight esters/acids/derivatives are used to form a wax composition having similar properties to beeswax, Montan wax, Carnauba wax, Candelilla wax, or Ouricury wax. In certain embodiments, the transesterified products 72 include ester compounds having hydrocarbon chain lengths greater than C18, C18 to C100, C22 to C60, C22 to C36, C28 to C32, or C40 to C52. In certain embodiments, the transesterified products 72 include at least 10 wt %, 20 wt %, 30 wt %, 40 wt %, 50 wt %, 60 wt %, 70 wt %, 80 wt %, or 90 wt % high-weight esters, high-weight acids, and/or high-weight derivatives thereof.

Alternatively, where the transesterified products 72 have not already been subjected to a cross-metathesis reaction with an olefin to extend the chain length of the hydrocarbons, the transesterified products 72 may be cross-metathesized with an olefin 74 in the presence of a metathesis catalyst to form a transesterified product including high-weight esters/acids/derivatives 76. The olefin 74 may be selected from the group including low-weight olefins, mid-weight olefins, high-weight olefins, and combinations thereof. In some embodiments, as noted above, the olefin stream 74 may be derived from the olefins 32 from the separation unit 30 or a downstream unit of the separation unit (e.g., partially or selectively hydrogenated olefins). In some embodiments, the olefin bottoms or heavier weight olefins (e.g., C14+, C16+, C18+, C16-C100, C16-C26, C20-C24, C22-C60, C24-C36, C28-C32, or C40-C52 olefins) may be used as the olefin stream 74 for the cross-metathesis reactant with the transesterified products 72. It is possible to use a mixture of low-weight, mid-weight, or high-weight olefins in the reaction to achieve the desired metathesis product distribution. In certain embodiments, the olefin feedstock 14 includes a mixture of C14-C36 olefins. In one embodiment, the olefin feedstock 14 includes a mixture of C14-C36 alpha-olefins.

In certain embodiments, the transesterified products 72 are cross-metathesized with a low-weight olefin in a metathesis reactor 75. In some embodiments, the low-weight olefin includes unsaturated straight, branched, or cyclic hydrocarbons in the C2 to C14 range, C4 to C10 range, or C11 to C14 range. In some embodiments, the low-weight olefin is an alpha-olefin.

In certain embodiments, the transesterified products 72 are cross-metathesized with a mid-weight olefin. In some embodiments, the mid-weight olefin includes unsaturated straight, branched, or cyclic hydrocarbons in the C15 to C24 range. In some embodiments, the mid-weight olefin is an alpha-olefin. In some embodiments, the mid-weight olefin is an alpha-olefin selected from the group including 1-pentadecene, 1-hexadecene, 1-heptadecene, 1-octadecene, 1-nonadecene, 1-icosene, 1-henicosene, 1-tricosene, 1-tetracosene, and combinations thereof. In one particular embodiment, the mid-weight olefin is 1-octadecene.

In other embodiments, the transesterified products 72 are cross-metathesized with a high-weight olefin. In certain embodiments, the high-weight olefin includes straight, branched, or cyclic hydrocarbons in the C25+, C25-C100, or C25-C36 range. In some embodiments, the high-weight olefin is an alpha-olefin. In some embodiments, the high-weight olefin is an alpha-olefin selected from the group including 1-pentacosene, 1-hexacosene, 1-heptacosene, 1-octacosene, 1-nonacosene, 1-triacontene, 1-hentriacontene, 1-dotriacontene, 1-tritriacontene, 1-tetratricontene, 1-pentatriacontene, 1-hexatriacontene, and combinations thereof.

In certain embodiments, the transesterified products 72 or transesterified products including high-weight esters, acids, and/or derivatives 76 can be sent to a liquid-liquid separation unit, wherein the products (e.g., high-weight esters/acids/derivatives, FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 70 for further processing. In other embodiments, the products from the reaction mass are further separated into the various individual components to be used separately or in conjunction with regard to final end uses.

In certain embodiments, the transesterified products 72 or transesterified products including high-weight esters/acids/derivatives 76 can be sent to a hydrogenation unit for selective hydrogenation, wherein the concentration of monounsaturated esters is increased by diene-selective hydrogenation. Certain reaction conditions, such as temperature, pressure, time of reaction, and hydrogenation catalyst type, are described above with regard to selective hydrogenation of the metathesis product 22.

In certain embodiments, in the diene selective hydrogenation, the conversion rate from the transesterified polyunsaturated esters/acids to saturated and monounsaturated transesterified esters/acids may be at least 50%, at least 75%, at least 85%, at least 95%, or at least 98%. The selectivity towards the monounsaturated esters/acids instead of saturated esters/acids is at least 90%, at least 95%, at least 99%, or at least 99.5%.

In one embodiment, the transesterified products 72 or transesterified products including high-weight esters/acids/derivatives 76 are further processed in a water-washing unit. In this unit, the transesterified products undergo a liquid-liquid extraction when washed with water. Excess alcohol, water, and glycerin are removed from the transesterified products. In another embodiment, the water-washing step is followed by a drying unit in which excess water is further removed from the desired mixture of high-weight esters/acids or specialty chemicals (e.g., 9DA, 9UDA, and/or 9DDA).

In certain embodiments, the transesterified products 72 or transesterified products including high-weight esters/acids/derivatives 76 or specialty chemicals from the water-washing unit or drying unit are sent to an ester distillation column 80 for further separation of various individual or groups of compounds, as depicted in FIGS. 1 and 2. This separation may include, but is not limited to, the separation of 9DA esters, 9UDA esters, and/or 9DDA esters. In one embodiment, the 9DA ester 82 may be distilled or individually separated from the remaining mixture 84 of transesterified products or specialty chemicals. In certain process conditions, the 9DA ester 82 may be the lightest component in the transesterified product or specialty chemical stream, and come out at the top of the ester distillation column 80. In another embodiment, the remaining mixture 84, or heavier components, of the transesterified products or specialty chemicals may be separated off the bottom end of the column. In certain embodiments, this bottoms stream 84 may potentially be sold as biodiesel. In certain embodiments, the heavier components (those not readily distilled) can be further separated using a variety of techniques known to those familiar with the art, including but not limited to, absorptive separation (e.g., simulated moving bed separation), solvent extraction, or fractional crystallization.

In certain embodiments, specific ester products, such as 9DDA methyl ester, may be enriched through subsequent processing and reaction steps of the transesterified products. In one embodiment, a C10 methyl ester stream may be separated from heavier C12+ methyl esters. The C10 methyl ester stream may then be reacted with 1-butene in the presence of a metathesis catalyst to form C12 methyl esters and ethylene. The ethylene may be separated from the methyl esters and the C10 and C12 methyl esters may be removed or returned to an ester distillation column for further processing.

In other embodiments, where the transesterified products 72 include high-weight esters/acids/derivatives, the distillation column may include the separation of the lighter components from the heavier, chain extended ester, acid, and derivative components.

In certain embodiments, the high-weight esters and/or high-weight acids from the transesterified products are isomerized to form isomerized high-weight esters and/or high-weight acids. The isomerization of the esters and/or acids may be conducted at an elevated temperature (e.g., greater than 25° C.). In certain embodiments, the temperature of the heat treatment for the isomerization reaction is greater than 100° C., greater than 150° C., or greater than 200° C. In other embodiments, the temperature is 100° C.-300° C., 150-250° C., or 200° C. In some embodiments, the heat treatment step is conducted in the presence of an isomerization catalyst. In one particular embodiment, the isomerization catalyst is $(PCy_3)_2(Cl)(H)Ru(CO)$, where "Cy" represents a cyclohexyl group.

Isomerized high-weight esters and/or isomerized high-weight acids may be used in a variety of different commercial applications, including, but not limited to: personal care products, structurants, emollients, lubricants, waxes, films, paints, paint strippers, coatings, plasticizers, resins, binders, solvents, polyols, soil stabilization, chemical grouting, chemicals for oil recovery, oilfield drilling fluids, crop protection products, surfactants, intermediates, and adhesives. Isomerizing the high-weight esters and/or high-weight acids may improve various performance properties. For example, the isomerized product composition may have an observed broadening of the freezing and melting points, which may allow for transportation of the high-weight esters and/or high-weight acids at higher concentrations of the high-weight esters and/or high-weight acids without incurring shipping problems. In certain embodiments, the isomerized high-weight esters/acids may help achieve the desired or improved sensory properties for a personal care application.

In certain embodiments, the isomerized high-weight acid, isomerized high-weight ester, high-weight acid, and/or high-weight ester is partially or fully hydrogenated. The partial to full hydrogenation of the esters/acids may enhance the thermal oxidative stability of the compound(s). Hydrogenation reaction conditions and catalysts are discussed above. In one particular embodiment, the hydrogenation reaction is conducted in the presence of a nickel based catalyst at approximately 150° C. and 150 psig. In another embodiment, the hydrogenation reaction is conducted in the presence of a nickel based catalyst at approximately 150° C. and 100 psig. In certain embodiments, these materials are selectively hydrogenated to increase the concentration of mono-unsaturated compounds. The partially or fully hydrogenated high-weight esters/acids and/or isomerized high-weight esters/acids may also be used in a variety of different commercial applications, including those uses mentioned in the paragraphs above.

Figure 3:
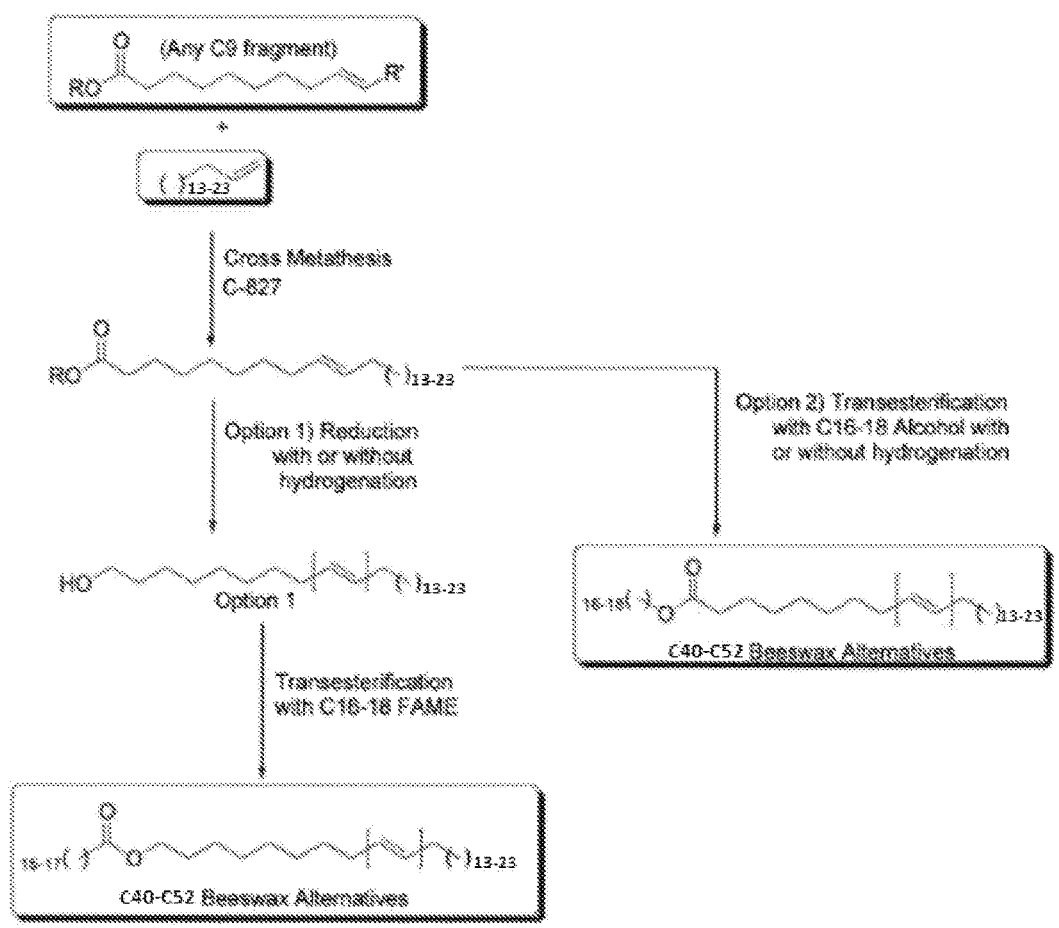
FIG. 3 depicts a schematic diagram of processes to produce beeswax-like high-weight ester compositions.

In some embodiments, as depicted in FIG. 3, a C40-C52 or C44-C50 beeswax-like composition may be formed through cross-metathesis, transesterification, and optionally, reduction reaction mechanisms. As depicted in FIG. 3, in one option, a natural oil or a natural oil derivative including fatty acid esters is cross-metathesized with a C16-C26 or C20-C24 alpha-olefin to form an extended chain or high-weight ester. The ester is also reduced (with or without an additional partial to full hydrogenation step) to form an alcohol. After cross-metathesis and hydrolysis, the resulting extended-chain, high-weight alcohol is transesterified with a C16-C18 fatty acid methyl ester to form a C40-C52 or C44-C50 ester composition useful in a beeswax-like composition. It is noted that, although not shown, the order of the transesterification, cross-metathesis, and hydrolysis reactions may be alternated (e.g., hydrolysis and/or transesterification steps may precede the cross-metathesis step).

Under a second option, also depicted in FIG. 3, the natural oil or natural oil derivative including a fatty acid ester component is cross-metathesized with a C16-C26 or C20-C24 alpha-olefin to form an extended chain or high-weight ester. The high-weight ester is then transesterified with a C16-C18 alcohol (with or without an additional partial to full hydrogenation step) to form the C40-C52 or C44-C50 ester composition. Again, the order between the cross-metathesis and transesterification steps may be alternated.

As noted, self-metathesis of the natural oil and cross-metathesis between the natural oil and the olefin feedstock occurs in the presence of a metathesis catalyst. As stated previously, the term "metathesis catalyst" includes any catalyst or catalyst system that catalyzes a metathesis reaction. Any known or future-developed metathesis catalyst may be used, individually or in combination with one or more additional catalysts. In some embodiments, the metathesis catalyst includes a transition metal. In some embodiments, the metathesis catalyst includes ruthenium, rhenium, tantalum, nickel, tungsten, or molybdenum. Non-limiting exemplary metathesis catalysts and process conditions are described in WO2009/020667, incorporated by reference herein. A number of the metathesis catalysts as shown are manufactured by Materia, Inc. (Pasadena, Calif.). The metathesis process can be conducted under any conditions adequate to produce the desired metathesis products, such as those described in U.S. Patent Application Publication Nos. 2011/0113679 and 2013/0085288. In certain embodiments, the metathesis reaction can conducted under conditions wherein at least a portion of the metathesized products (or byproducts) are removed as they are produced, thus shifting the equilibrium toward the formation of more product (e.g., using a vacuum during the reaction).

In certain embodiments, the high-weight esters/acids/derivatives may be blended with additional fatty acids having from 6 to 24 carbon atoms, including, but not limited to, caproic acid, caprylic acid, capric acid, lauric acid, myristic acid, palmitic acid, oleic acid, linoleic acid, linolenic acid, stearic acid, arachidic acid, erucic acid, lignoceric acid, behenic acid, and nervonic acid.

In certain embodiments, the high-weight esters/acids/derivatives may be blended with the olefin byproduct from the metathesis reactions. In other embodiments, the high-weight esters/acids/derivatives may be blended with paraffin or other hydrocarbon compounds.

In certain embodiments, the high-weight esters and acids may be used in a wax composition or personal care product. For example, the high-weight esters or acids may be used in a beeswax-like composition, Montan wax-like composition, Carnauba wax-like composition, Candelilla wax-like composition, or Ouricury Wax-like composition. In some embodiments, the high-weight ester or acid includes more than 50 wt %, 50-90 wt %, 60-80 wt %, or 65-75 wt % of the wax composition.

In one embodiment, the high-weight esters/acids/derivatives are blended with other components to form a personal care composition, such as a lotion. The composition may be blended in various phases. The overall composition may include blending:

(1) 1-40 wt %, 5-25 wt %, or 8-10 wt % of the high-weight ester/acid/derivative (e.g., canola oil cross-metathesized with a C18 LAO);
(2) 0.1-5 wt % or 2-4 wt % fatty acid (e.g., stearic acid);
(3) 0.1-5 wt % or 2-4 wt % glycerides (e.g., glycerol stearate and/or PEG-100 stearate);
(4) 0.1-2 wt % or 1 wt % silicone-based polymer (e.g., a siloxane such as dimethicone);
(5) 50-80 wt %, 65-75 wt %, or 68-70 wt % water;
(6) 0.1-10 wt %, 2-6 wt % or 4 wt % glycerin;
(7) 0-5 wt %, 0.1-2 wt %, or 0.5-1 wt % amines or weak base (e.g., triethanolamine);
(8) 0.1-25 wt %, 5-15 wt %, or 10 wt % carbomer or polyacrylic acid; and
(9) 0-5 wt %, 0.01-2 wt %, or 0.1-1 wt % preservatives (e.g., hydantoin).

In some embodiments, the high-weight ester/acid/derivative is blended in one phase with the fatty acid, glycerides, and silicone-based polymer, while a second phase includes blending the water, glycerin, and amines/weak base.

In another embodiment, the high-weight esters/acids/derivatives are blended with other components to form an elastomer-like composition. The overall composition may include blending (1) 1-99 wt %, 10-40 wt %, 20-35 wt %, or 25-30 wt % of the high-weight ester/acid/derivative (e.g. canola oil cross-metathesized with a C18 LAO); and (2) 1-99 wt %, 50-90 wt %, 60-80 wt %, or 70-75 wt % paraffin (e.g., C4-C22, C10-C18, or C12-C13 paraffin).

In certain embodiments, the wax-like composition is a beeswax-like composition, which may be used in a wide variety of applications such as personal care products, cosmetics, pharmaceutical preparations, polishes (car, shoes, and floors), and candle making. The beeswax like composition may include a mixture of high-weight esters, hydrocarbons, and free fatty acids. In some embodiments, the beeswax composition includes 60-80 wt % C40-C52 or C44-C50 high-weight esters, 10-20 wt % hydrocarbons, and 5-20 wt % free fatty acids. In one embodiment, the beeswax composition includes approximately 70 wt % C40-C52 or C44-C50 high-weight esters, approximately 14 wt % hydrocarbons, and approximately 12 wt % free fatty acids.

In certain embodiments, the wax composition having the high-weight esters or acids may have a drop point 122° F.-266° F. (50° C. and 130° C.), 131° F.-212° F. (55° C.-100° C.), 142° F.-151° F. (61° C.-66° C.), 150° F.-200° F. (66° C.-93° C.), 170° F.-190° F. (77° C.-88° C.), 176° F.-185° F. (80° C.-85° C.), 208-210° F. (98-99° C.), or 160° F.-194° F. (71° C.-90° C.). In some embodiments, the wax has a needle penetration of 0-30 dmm, 0-20 dmm, 10 dmm or less, 5 dmm or less, or 2-4 dmm at 25° C. (77° F.). In certain embodiments, the wax has a saponification value of greater than 50 mg KOH/g, 50-250 mg KOH/g, 150-250 mg KOH/g, or 190-250 mg KOH/g.

In other embodiments, the wax has an acid value 1-270 mg KOH/g, 1-150 mg KOH/g, 1-100 mg KOH/g, or 10-50 mg KOH/g. The color of the wax may be white, cream to light tan, or yellow to dark brown.

The methods of making the compositions including high-weight esters/acids/derivatives may include methods of blending or mixing in an effort to target end products having specific properties such as the composition's sensory/textural properties or crystalline structure to facilitate a slippery or smooth feel. For example, the high-weight esters/acids/derivatives may be blended with the olefin byproducts formed through the metathesis reactions (e.g., C10-C18 olefins) to adjust the physical properties of the end, commercial product. In other embodiments, the high-weight esters/acids/derivatives are blended with paraffin (e.g., C12-C13 paraffin) or other hydrocarbon compounds and/or with free fatty acids to adjust the composition properties. In yet other embodiments, the end properties of the composition may be adjusted by varying the stoichiometry of the various metathesis or esterification reactants.

Further, the physical properties of the end product may be modified and enhanced through "votation" or agitation of the high-weight esters/acids/derivative product composition (which may include additional product such as the olefin byproduct, paraffin, etc.). For example, it has also been found that end product including the high-weight esters/acids/derivatives may have enhanced sensory properties (e.g., observed by applying or spreading on the skin), which make the products particularly useful for application in the personal care market.

The votation process on the high-weight ester/acid/derivative may be implemented to further improve the crystalline structure of the overall composition. In certain embodiments, the votation process involves super-cooling and then plasticizing the composition to form the targeted the desired crystal structure through controlled agitation to develop a potentially less-rigid structure, and softer composition as measured by needle penetration. In some embodiments, the crystalline structure may be controlled through cooling the reactant mixture from an elevated metathesis reaction temperature to ambient temperature (e.g., 20-25° C.) over the period of 1 min, 5 min, 10 min, 15 min, 30 min, or 60 min. The reactant mixture having the high-weight esters/acids/derivatives are agitated for at least a portion of the time that the composition is cooled to ambient temperature.

In some embodiments, the votation process is carried out using a scraped surface heat exchanger (SSHE). SSHEs may be a tubular heat exchanger cooled by a liquid refrigerant (e.g., ammonia) with scraper blades mounted on the central shaft that rotates continuously, removing crystalized fat from the inner tube of the heat exchanger to promote rapid cooling and crystal nucleation in a short residence time (seconds). SSHEs may work in combination with crystallizer units, which hold a larger volume and have a longer residence time (e.g., several minutes). These units work the product between a series of metal pins fixed to the crystallizer tube and others mounted on a rotating central shaft, shearing the product, preventing formation of large crystal networks.

While the invention as described may have modifications and alternative forms, various embodiments thereof have been described in detail. It should be understood, however, that the description herein of these various embodiments is not intended to limit the invention, but on the contrary, the intention is to cover all modifications, equivalents, and alternatives falling within the spirit and scope of the invention as defined by the claims. Further, while the invention will also be described with reference to the following non-limiting examples, it will be understood, of course, that the invention is not limited thereto since modifications may be made by those skilled in the art, particularly in light of the foregoing teachings.

EXAMPLES

Example 1

A flask was charged with methyl-9-dodecenoate (50 g, 0.235 mol) and 1-octadecene (59.5 g, 0.235 mol). The solution was purged with $N_2$ as it was heated to 180° C. The purge was continued and the temperature is held for 2 hours. The solution was cooled to room temperature overnight under $N_2$. The flask was fitted with a distillation condenser and placed under 500 mmHg vacuum. After warming the solution to 70° C., a solution of 40 ppm C827 metathesis catalyst in toluene was added (110 uL). After about 5 minutes, vigorous bubbling was observed, which then decreases over 90 minutes. A second addition of C827 solution (110 uL) was charged to the reaction, however, no gas evolution was observed. The reaction continued for a total of 180 minutes and then allowed to cool to room temperature. The cooled material solidified into a soft waxy substance. This solidification is indicative of forming the higher molecular weight species (diester, higher weight mono-ester and some higher molecular weight hydrocarbon.

Example 2

A flask was charged with C13-C15 methyl esters derived from a metathesis reactions of seed oils and having significant amounts of unsaturation (57 g, ~0.235 mol, simulated fraction from metathesis and transesterification of palm oil) and 1-octadecene (59.5 g, 0.235 mol). The solution was purged with $N_2$ as it was heated to 200° C. The purge was continued and the temperature was held for 1.5 hours. The flask was fitted with a distillation condenser, cooled to 70° C., and then placed under 500 mmHg vacuum. A solution of 40 ppm C827 in toluene was added (110 uL) to the solution. No obvious gas evolution was observed. After 90 minutes, a second addition of C827 solution was charged, and the reaction was continued for a total of 180 minutes. Upon cooling to room temperature, the material became semi-solid.

Example 3

1-octadecene (88.73 g) was combined with butenolized canola triacyl glyceride (metathesized TAG; 32.34 g) in a round bottom flask. The liquid mixture was sparged with dry nitrogen and stirred magnetically while being heated 200° C. The mixture was then held at these conditions (stirring and sparging at 200° C.) for 2 hours before being allowed to cool while maintaining an inert atmosphere. Once the mixture had cooled below 50° C., 12.1 mg Materia C827 metathesis catalyst was added to the mixture. The catalyst was transferred by using 1 mL of the reaction mixture to slurry the dry catalyst and another 1 mL of the reaction mixture to rinse the residual catalyst slurry into the reaction vessel. The reaction mixture was then heated to 70° C. under an inert atmosphere and held at these conditions for 2 hrs. At this point the reaction mixture was allowed to cool to ambient temperature and stored overnight under and inert atmosphere (16 hrs).

The next morning, the reaction mixture, which was now a solid at ambient temperature, was heated to 70° C. causing it to melt. Once the mixture had completely melted, it was charged with an additional 12.1 mg catalyst using the same technique as previously described. The reaction was allowed to proceed at 70° C. for 3 hrs before the temperature was ramped up to 300° C. under 1 Torr vacuum. The stripping took a total of 90 min and left a light brown buttery solid in the pot.

The pot bottoms, largely composed of triacylglyceride esters, were sampled and transesterified using sodium methoxide and methanol to produce the corresponding methyl esters for analysis by gas chromatography mass spectroscopy. Analysis of the resulting fatty acid methyl esters showed approximate concentrations of 40 mol % C26 monoester, 3 mol % C28 monoester, and 6 mol % C18 diester.

Example 4

A hydrogenated, extended-chain ester was formed from the cross-metathesis of a canola oil and C18 linear alpha olefin (LAO). The extended-chain ester was blended with additional components to form a product with potentially use to petrolatum as a humectant. This blended product also has some film forming properties that might be observed in a lotion. The overall composition included:

| Material: | Wt % | Wt (g) | Lot Number |
|---|---|---|---|
| Phase A: | | | |
| Stearic Acid | 3.0 | 12.04 | Emersol 132 NF V21C09J037 |
| Glyceryl Stearate (and) PEG-100 Stearate | 3.0 | 21.04 | Lipomulse 165 P-2238l11 |
| Dimethicone (1000 cSt) | 1.0 | 4.10 | I-Sil 1,000 111908D |
| Canola CM C18 LAO (MCO) | 9.0 | 36.80 | 1150-52-$H_1$ |
| Phase B: | | | |
| Water | 69.1 | 276.80 | DI |
| Glycerin | 4.0 | 40.0 | 16492-120619 |
| Triethanolamine | 0.6 | 2.44 | Dow B2139 |
| Carbomer: | | | |
| Carbomer (.1% dispersion) | 10.0 | 16.16 | 1130-150 |
| Preservative: | | | |
| DM DM Hydantoin | 0.3 | | Glydant M1436241 |

Procedure:

Phase B was weighed in a 600 mL and then placed into a 2 L jacketed glass beaker that was heated to 80° C. using an aqueous glycol circulating bath. A mechanical stirrer was placed into the beaker. The carbomer was weighed out into a 50 mL beaker and then covered until ready for use. Phase A was weighed out into a 150 mL glass beaker and placed into a 75° C. oven to melt. The molten Phase A was stirred and added to Phase B at 65° C. while being mechanically stirred. Once a uniform dispersion was observed, the carbomer was added. The mixture was stirred for 10 min. The circulating fluid was changed from 80° C. to −10° C. to cool the mixture to ambient temperature. The cream was transferred into a glass jar (500 mL) where the DM DM hydantoin was added. It was thoroughly mixed in using a metal spatula.

Example 5

An extended-chain ester was formed and blended with paraffin and compared with silicon elastomers having similar paraffin content.

| Material | Wt % | Wt (g) | Lot |
|---|---|---|---|
| Canola MTAG/C18 LAO CM | 27.4 | 12.58 | 1150-52-$H_1$ |
| C12/C13 (99%/<1%) Paraffin | 72.6 | 33.38 | 1045-88-A |

Procedure:

Solid Elastomer was weighted into a 100 mL glass beaker and diluted to a relatively low-viscosity paste by the portion wise addition of C12 Paraffin. This was placed into a glass jar. The hydrogenated product of a C18 linear alpha olefin (LAO) and canola oil cross metathesis was weighed out in a similar fashion and placed into a 100 mL glass jar. The jar was placed into a 75° C. oven for 30 min until the entire mixture had melted. The mixture was stirred to homogenize the solution then the jar was allowed to cool to ambient temperature. The warm liquid was warm but as it cooled it became a white opaque gel. This is in contrast to the behavior of most heavy waxes which, under these conditions, would separate out from the light paraffin solvent (dodecane). The metathesis product, however, swelled to structure the solvent and form a homogenous gel. The feel of the two materials was compared.

What is claimed is:

1. A method of making high-weight esters, high-weight acids, or high-weight derivatives thereof, comprising:
    providing a starting feedstock comprising unsaturated fatty acid esters or unsaturated fatty acids, wherein a majority of the fatty acid chain lengths in the feedstock are less than or equal to C24;
    optionally hydrolyzing the unsaturated fatty acid esters in the starting feedstock to form a hydrolyzed feedstock comprising hydrolyzed unsaturated fatty acids;
    optionally transesterifying the unsaturated fatty acid esters or the unsaturated fatty acids of the starting feedstock or the hydrolyzed unsaturated fatty acids of the hydrolyzed feedstock to form a transesterified feedstock comprising transesterified unsaturated fatty acid esters;
    cross-metathesizing the unsaturated fatty acid esters or the unsaturated fatty acids of the starting feedstock, the hydrolyzed unsaturated fatty acids of the hydrolyzed feedstock, or the transesterified unsaturated fatty acid esters of the transesterified feedstock with an olefin feedstock in the presence of a metathesis catalyst, thereby forming a metathesized product comprising high-weight fatty acid esters or high-weight fatty acids having fatty acid chain lengths greater than C18, wherein at least a portion of the fatty acid chain lengths in the metathesized product are larger than the fatty acid chain lengths in the starting feedstock; and
    either (i) reducing the high-weight fatty acid esters or the high-weight fatty acids to form a high-weight alcohol, or (ii) transesterifying the high-weight fatty acid esters or the high-weight fatty acids with an alcohol.

2. The method of claim 1, comprising reducing the high-weight fatty acid esters or the high-weight fatty acids to form a high-weight alcohol.

3. The method of claim 2, further comprising transesterifying the high-weight alcohol with a fatty acid ester.

4. The method of claim 3, wherein the starting feedstock comprises an unsaturated fatty acid ester having an unsaturated carbon-carbon bond at the C9-C10 position of the unsaturated fatty acid ester, wherein the olefin feedstock comprises a mixture of C16-C26 alpha-olefins, such that the metathesized product comprises a C24-C34 fatty acid ester, which is reduced to a C24-C34 alcohol, which is reacted with a C16-C18 fatty acid methyl ester, thereby forming a C40-C52 high-weight ester composition.

5. The method of claim 4, further comprising blending the C40-C52 high-weight ester composition with a hydrocarbon feedstock and a free fatty acid feedstock, thereby forming a beeswax-like composition.

6. The method of claim 1, comprising transesterifying the high-weight fatty acid esters or the high-weight fatty acids with an alcohol to form transesterified high-weight fatty acid esters.

7. The method of claim 6, wherein the starting feedstock comprises an unsaturated fatty acid ester having an unsaturated carbon-carbon bond at the C9-C10 position of the unsaturated fatty acid ester, wherein the olefin feedstock comprises a mixture of C16-C26 alpha-olefins, such that the metathesized product comprises a C24-C34 fatty acid ester, which is transesterified to a transesterified C24-C34 fatty acid, which is reacted with a C16-C18 alcohol, thereby forming a C40-C52 high-weight ester composition.

8. The method of claim 7, further comprising blending the C40-C52 high-weight ester composition with a hydrocarbon feedstock and a free fatty acid feedstock, thereby forming a beeswax-like composition.

9. The method of claim 1, further comprising at least partially hydrogenating the high-weight fatty acid esters or the high-weight fatty acids.

* * * * *